(12) United States Patent
Wright et al.

(10) Patent No.: US 11,890,175 B2
(45) Date of Patent: Feb. 6, 2024

(54) ARTICLE WITH CHASSIS HAVING AN ELASTIC DISTRIBUTION, ABSORBENT CORE AND SYSTEM AND METHOD FOR MAKING SAME

(71) Applicant: DSG TECHNOLOGY HOLDINGS LTD., Kwai Chung (HK)

(72) Inventors: Andrew Wright, Rotherham (GB); Dennis Smid, Wolvega (NL); Anne Smid, Wolvega (NL); Eugenio Varona, Marietta, GA (US)

(73) Assignee: DSG Technology Holdings Ltd., Kwai Chung (HK)

( * ) Notice: Subject to any disclaimer, the term of this patent is extended or adjusted under 35 U.S.C. 154(b) by 171 days.

(21) Appl. No.: 17/234,154

(22) Filed: Apr. 19, 2021

(65) Prior Publication Data

US 2021/0307974 A1 Oct. 7, 2021

Related U.S. Application Data

(63) Continuation of application No. 15/903,008, filed on Feb. 22, 2018, now Pat. No. 10,993,849, which is a
(Continued)

(51) Int. Cl.
*A61F 13/15* (2006.01)
*A61F 13/49* (2006.01)
(Continued)

(52) U.S. Cl.
CPC .. *A61F 13/49019* (2013.01); *A61F 13/15593* (2013.01); *A61F 13/15609* (2013.01);
(Continued)

(58) Field of Classification Search
CPC .......... A61F 13/49019; A61F 13/15593; A61F 13/15609; A61F 13/15707;
(Continued)

(56) References Cited

U.S. PATENT DOCUMENTS

| 4,525,229 A | 6/1985 | Suzuki et al. |
| 5,147,487 A | 9/1992 | Nomura et al. |

(Continued)

FOREIGN PATENT DOCUMENTS

| EP | 0623331 A2 | 11/1994 |
| EP | 0962207 A2 | 12/1999 |

(Continued)

OTHER PUBLICATIONS

Extended EP Search Report, issued in EP Application No. 18757761.4 dated Nov. 9, 2020 [6 pages].
(Continued)

*Primary Examiner* — Jacqueline F Stephens
(74) *Attorney, Agent, or Firm* — Alberto Q. Amatong, Jr.; Amatong McCoy LLC

(57) ABSTRACT

An absorbent article may include an inner elasticised chassis. An opening may be formed through the inner elasticised chassis. The absorbent article may include an outer elasticised chassis, and an absorbent member located between the inner elasticised chassis and the outer elasticised chassis. The inner elasticised chassis may include sets of elastic strands surrounding the absorbent member. The opening may be located in a space between the sets of elastic strands.

23 Claims, 24 Drawing Sheets

Related U.S. Application Data continuation-in-part of application No. 14/946,528, filed on Nov. 19, 2015, now Pat. No. 10,045,887, which is a continuation of application No. 13/200,100, filed on Sep. 16, 2011, now Pat. No. 9,205,003.

(60) Provisional application No. 62/462,349, filed on Feb. 22, 2017, provisional application No. 61/403,488, filed on Sep. 16, 2010.

(51) Int. Cl.
| | |
|---|---|
| *A61F 13/496* | (2006.01) |
| *B32B 37/14* | (2006.01) |
| *B32B 37/20* | (2006.01) |
| *B32B 3/18* | (2006.01) |
| *B32B 37/02* | (2006.01) |

(52) U.S. Cl.
CPC .. *A61F 13/15707* (2013.01); *A61F 13/15723* (2013.01); *A61F 13/15747* (2013.01); *A61F 13/496* (2013.01); *A61F 13/49011* (2013.01); *A61F 13/49014* (2013.01); *A61F 2013/15715* (2013.01); *A61F 2013/49038* (2013.01); *A61F 2013/49092* (2013.01); *B32B 3/18* (2013.01); *B32B 37/02* (2013.01); *B32B 37/144* (2013.01); *B32B 37/203* (2013.01); *B32B 2555/02* (2013.01)

(58) Field of Classification Search
CPC .......... A61F 13/15723; A61F 13/15747; A61F 13/49011; A61F 13/49014; A61F 13/496; A61F 2013/15715; A61F 2013/49038; A61F 2013/49092; B32B 3/18; B32B 37/02; B32B 37/144; B32B 37/203; B32B 2555/02

See application file for complete search history.

(56) References Cited

U.S. PATENT DOCUMENTS

| | | | |
|---|---|---|---|
| 5,360,422 A | 11/1994 | Brownlee et al. | |
| 5,576,091 A | 11/1996 | Zajaczkowski et al. | |
| 5,613,959 A | 3/1997 | Roessler et al. | |
| 6,013,065 A * | 1/2000 | Suzuki | A61F 13/495 |
| | | | 604/385.27 |
| 6,248,098 B1 * | 6/2001 | Sayama | A61F 13/495 |
| | | | 604/385.27 |
| 6,391,013 B1 | 5/2002 | Suzuki et al. | |
| 6,491,676 B1 | 12/2002 | Suzuki et al. | |
| 6,520,945 B1 | 2/2003 | Hansson | |
| 6,638,262 B2 | 10/2003 | Suzuki et al. | |
| 6,713,661 B1 * | 3/2004 | Arndt | A61F 13/15203 |
| | | | 604/385.101 |
| 6,790,798 B1 | 9/2004 | Suzuki et al. | |
| 6,794,557 B1 | 9/2004 | Klemp et al. | |
| 7,361,246 B2 | 4/2008 | Chang et al. | |
| 7,462,172 B2 | 12/2008 | Wright et al. | |
| 8,083,724 B2 | 12/2011 | Bittner et al. | |
| 8,157,781 B2 | 4/2012 | Takino et al. | |
| 8,568,380 B2 | 10/2013 | Brownlee | |
| 8,785,715 B2 | 7/2014 | Wright et al. | |
| 9,205,003 B2 | 12/2015 | Tsang et al. | |
| 2002/0068919 A1 * | 6/2002 | Shinohara | A61F 13/49019 |
| | | | 604/385.27 |
| 2002/0143316 A1 | 10/2002 | Sherrod et al. | |
| 2003/0045855 A1 | 3/2003 | Ono et al. | |
| 2008/0033387 A1 | 2/2008 | Wastlund-Karlsson et al. | |
| 2009/0005751 A1 | 1/2009 | Shirai et al. | |
| 2009/0320993 A1 | 12/2009 | Yamamoto | |
| 2010/0078119 A1 | 4/2010 | Yamamoto | |
| 2010/0179496 A1 | 7/2010 | Roe et al. | |
| 2010/0179500 A1 | 7/2010 | Roe et al. | |
| 2011/0130736 A1 | 6/2011 | Tsang et al. | |
| 2016/0278999 A1 | 9/2016 | Wang et al. | |

FOREIGN PATENT DOCUMENTS

| | | |
|---|---|---|
| EP | 1300124 A2 | 4/2003 |
| JP | 2008061876 A | 3/2008 |

OTHER PUBLICATIONS

International Preliminary Report on Patentability issued in PCT Application No. PCT/US2018/019296, dated Jul. 29, 2019 [17 pages].

International Search Report dated Aug. 8, 2018, during the prosecution of International Application No. PCT/US2018/019296. [5 pages].

International Search Report dated May 5, 2016, during the prosecution of International Application No. PCT/US2016/019914. [3 pages].

Written Opinion dated Aug. 8, 2018, during the prosecution of International Application No. PCT/US2018/019296. [11 pages].

Written Opinion dated May 5, 2016, during the prosecution of International Application No. PCT/US2016/019914. [7 pages].

* cited by examiner

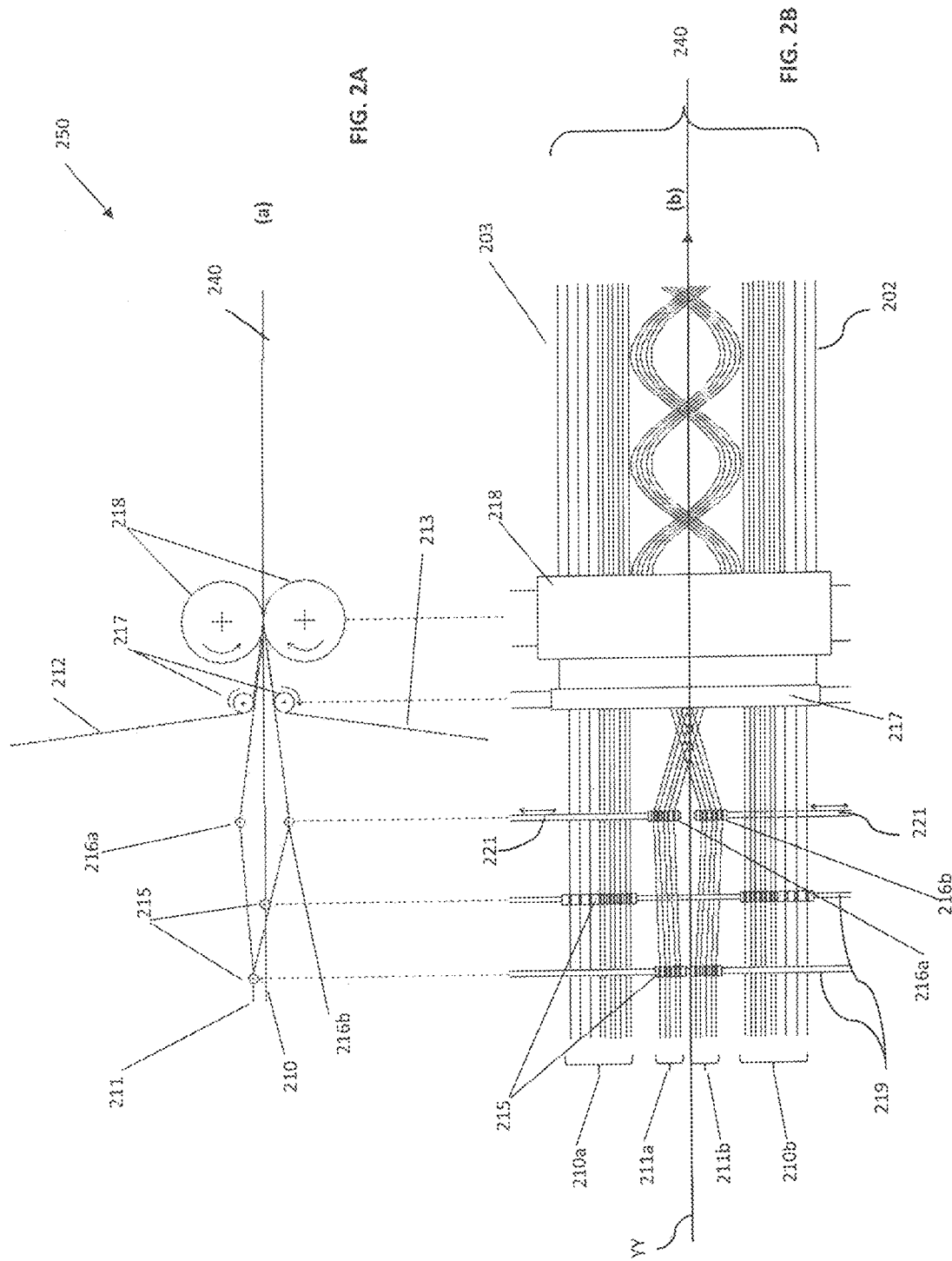

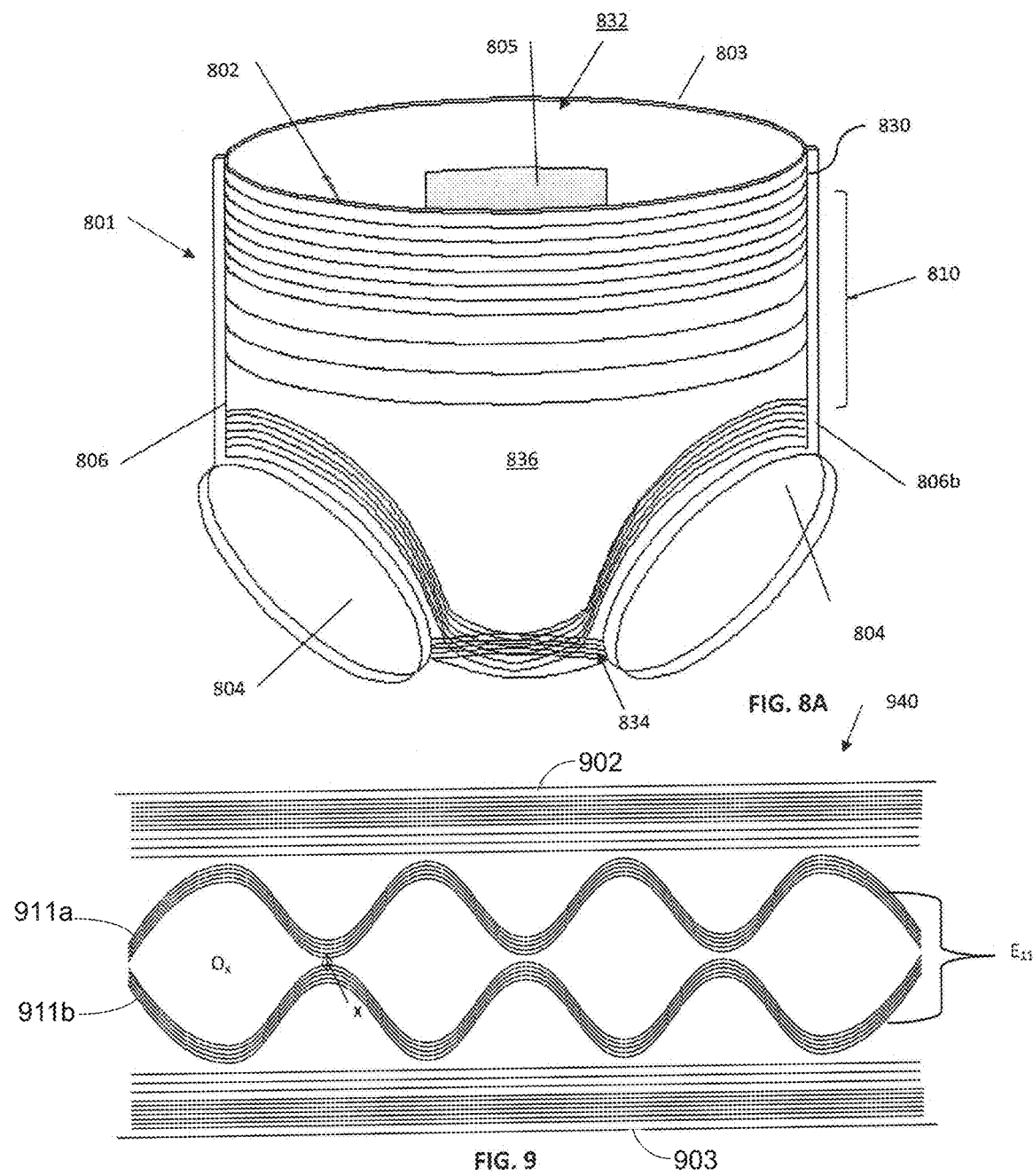

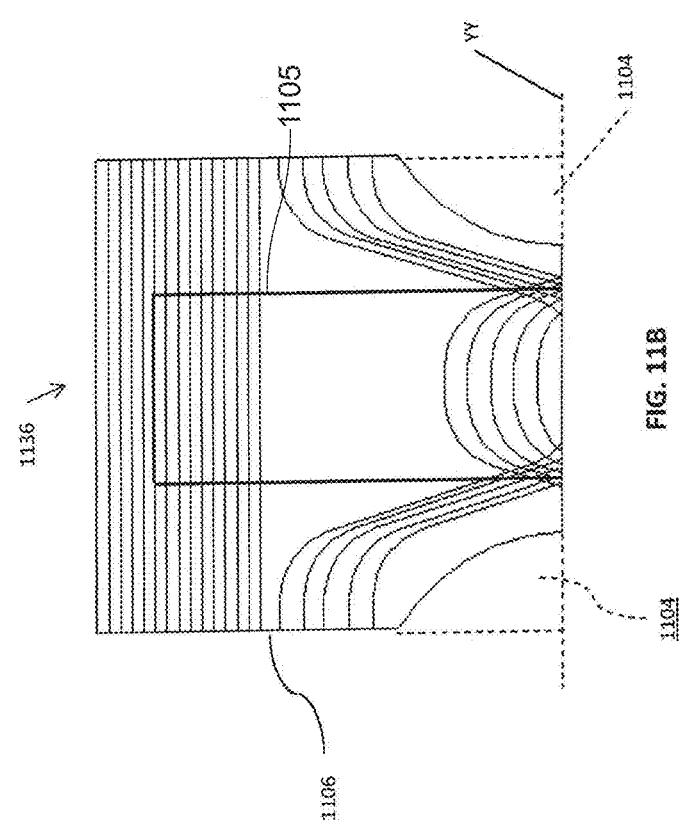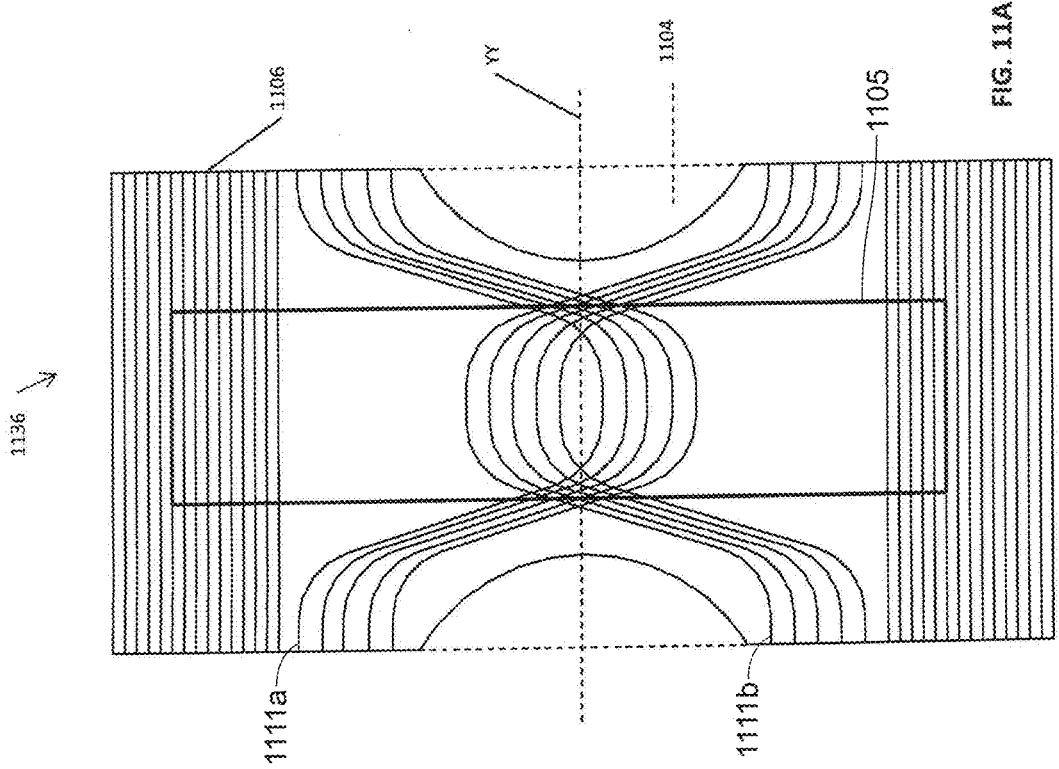

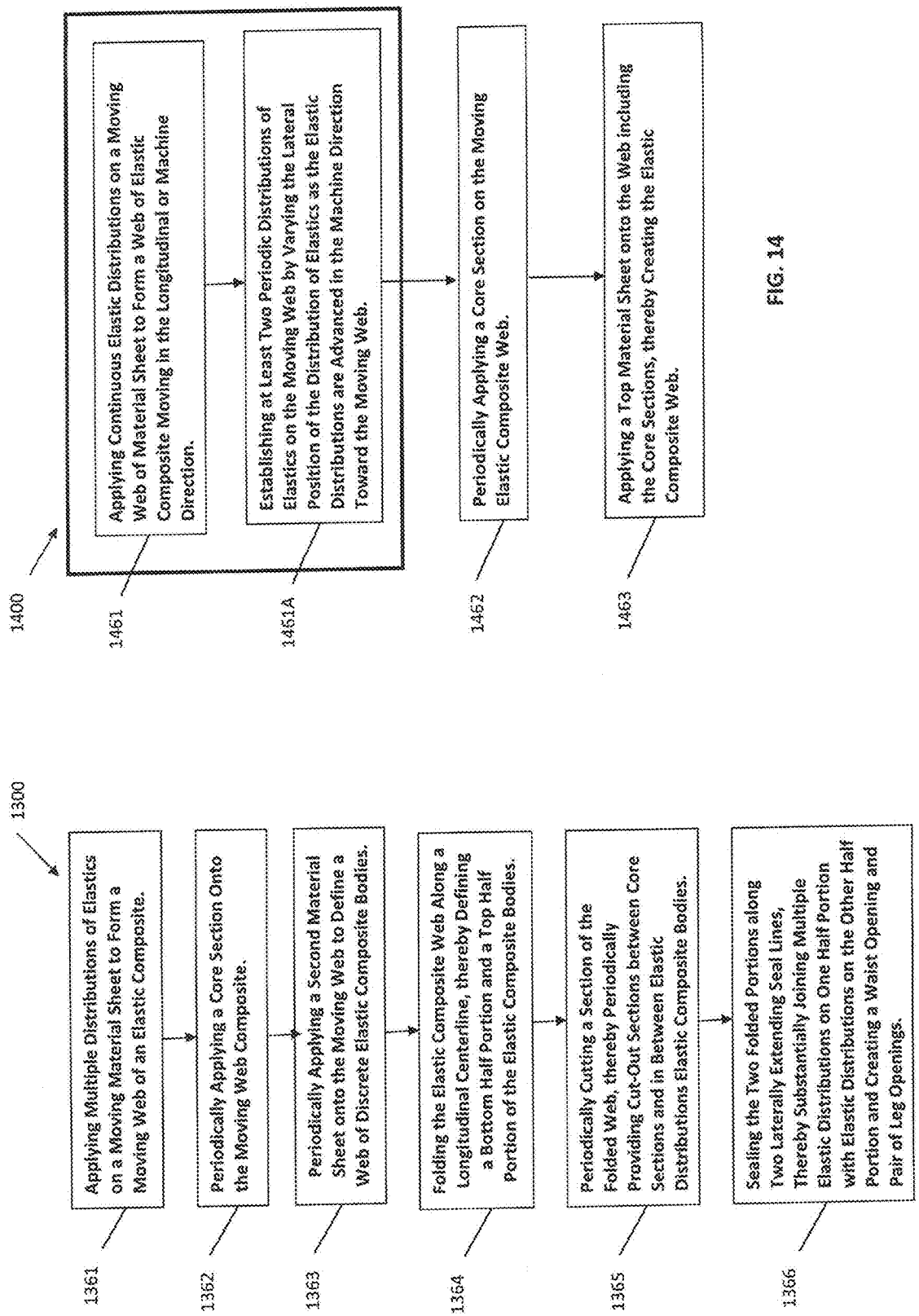

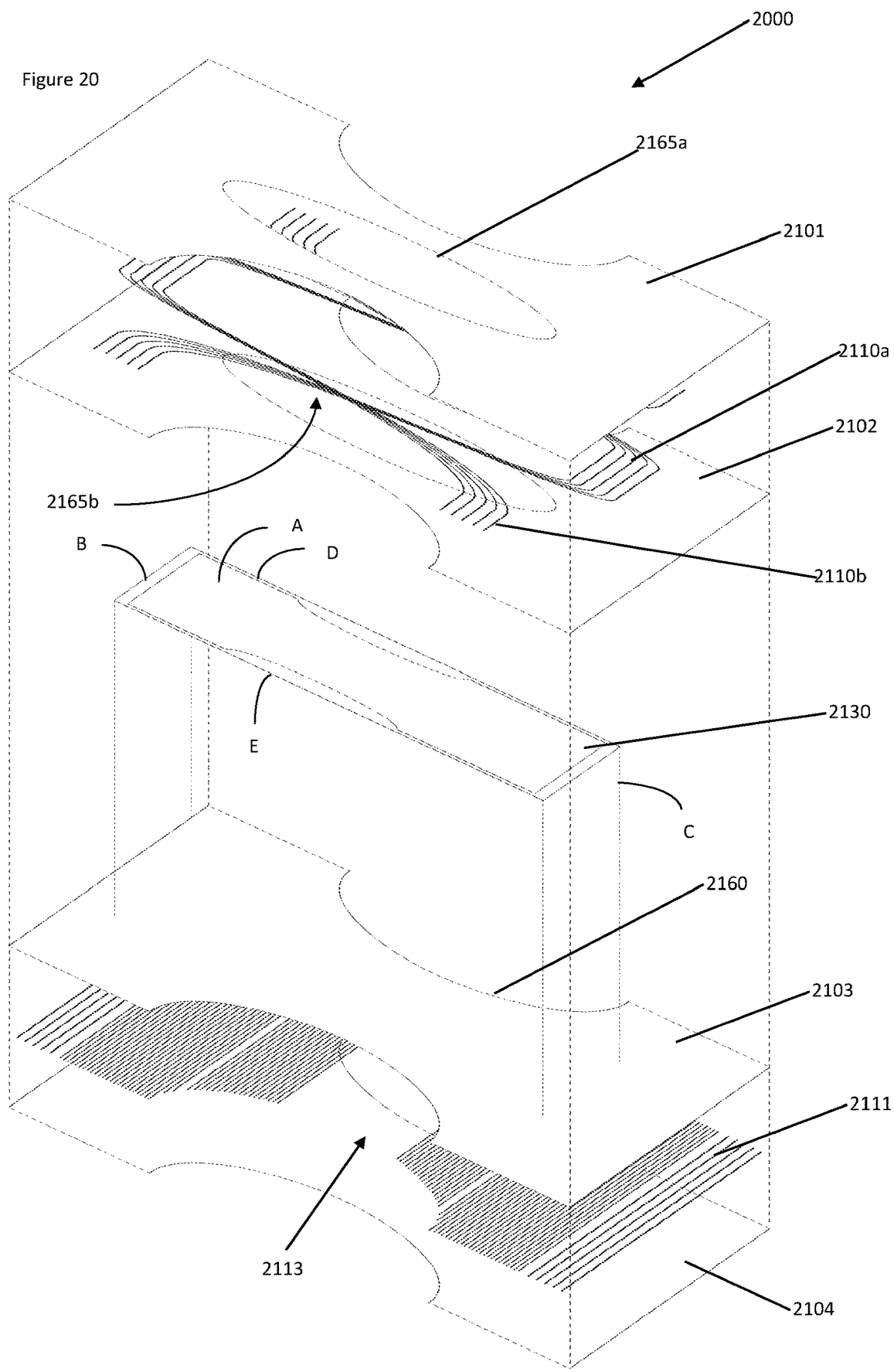

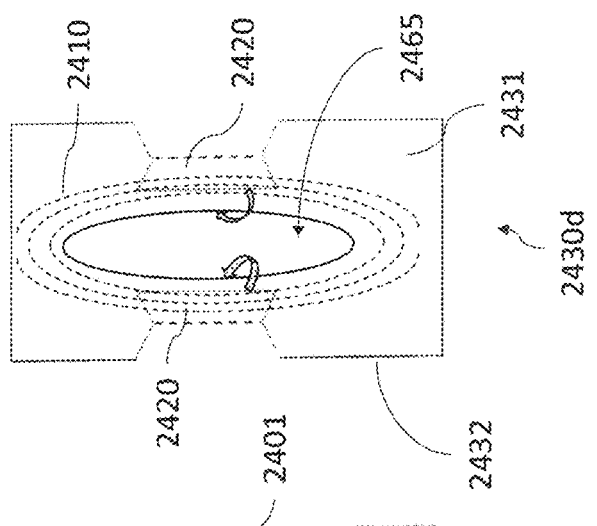
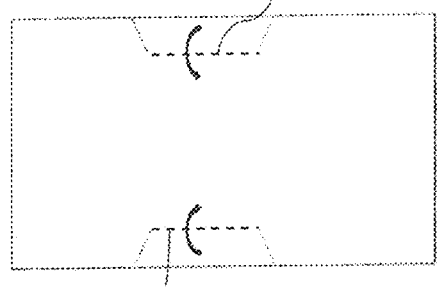
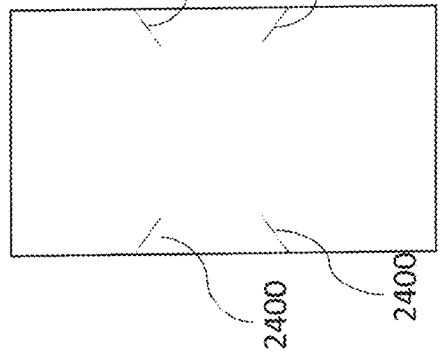
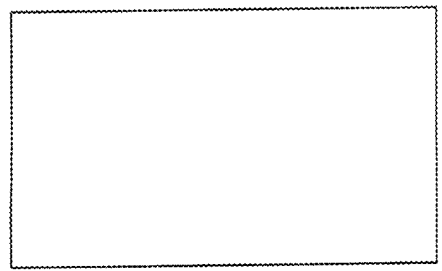

ARTICLE WITH CHASSIS HAVING AN ELASTIC DISTRIBUTION, ABSORBENT CORE AND SYSTEM AND METHOD FOR MAKING SAME

CROSS-REFERENCE TO RELATED APPLICATIONS

This present application is a Continuation application of U.S. application Ser. No. 15/903,008, filed Feb. 22, 2018 (now allowed), which claims priority to and the benefit of U.S. Provisional Patent Application No. 62/462,349, filed on Feb. 22, 2017, and also claims priority to and the benefit, as a Continuation-in-part (CIP) of U.S. patent application Ser. No. 14/946,528, filed on Nov. 19, 2015 (now issued as U.S. Pat. No. 10,045,887); which itself claims priority to, as a Continuation of, U.S. patent application Ser. No. 13/200,100, filed on Sep. 16, 2011 (now issued as U.S. Pat. No. 9,205,003); which itself claims priority to and the benefit of U.S. Provisional Patent Application 61/403,488, filed on Sep. 16, 2010; which disclosures are hereby incorporated by reference in their entireties and made a part of the present disclosure for all purposes.

FIELD

The present disclosure relates generally to an elastic composite, a core composite, and a disposable absorbent article incorporating an elastic composite and\or a core composite. The disclosure also relates to elastic composite webs, systems, and methods suitable for making the same. At least some aspects of the disclosure are particularly suited for, or related to, disposable absorbent articles such as baby diapers, training pants for infants and young children and adult incontinence diapers and pants. Some embodiments may provide a web of elastic composite, an elastic composite or body, or elastic distribution patterns within these products, which, in turn, may improve the product's fit and comfort, its support and sealing capabilities, and may enhance the cost and manufacturability of the product and\or enhance the aesthetic qualities of the product.

BACKGROUND

Disposable absorbent articles contemplated in this disclosure include, but are not limited to, training pants, pull-on diapers, disposable underwear, and adult incontinence garments. As for training pants, these garments may be used by young children to facilitate a child's transition from using diapers to wearing regular underpants (i.e., during toilet training). Training pants and other disposable pull-on pants may have closed sides such that the user or caregiver raises the garment about the user's legs to wear the garment and slips the garment downward about the user's legs to take it off. These articles and garments are collectively referred to herein as "absorbent pants" or "pants products."

Elastic members may be incorporated into different parts of an absorbent garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of an absorbent garment. The resulting elastication allows the garment to stretch when it is put on and when it is worn. The elastication allows the garment to accommodate variations in waist size and leg size of the user, while fitting snugly about the waist and legs.

When elastic members are incorporated into a part or area of an absorbent garment, that part or area typically becomes a distinct, functional component of the garment. These elastic components include the side panels or ear portions, the waistband, and fastening tabs. Due in part to its multi-component construction, elastic composites may require a dedicated sub-process for manufacture, which may be accommodated by the greater garment manufacturing process. The elastic composite may be manufactured independently, or may be manufactured in a separate sub-process detached from the central garment manufacturing system. In either case, a source of the elastic composite may be provided as input to the garment manufacturing process.

In some applications, the elastic composite may have a significant impact on the fit and sealability of the garment, as well as the general appearance and construction quality of the garment. The design and construction of the elastic composite may also represent a significant portion of the cost of manufacturing the garment. It is, therefore, desirable to provide a functionally and/or aesthetically improved elastic composite or a cost-effective system and method of making the elastic composite.

U.S. Pat. Nos. 7,462,172 and 7,361,246 provide background information on elastic composites (and the manufacture of such composites) of a type relevant to the present disclosure. Accordingly, these patent publications are hereby incorporated by reference and made a part of the present disclosure, but only to the extent that incorporated subject matter provides background information and/or exemplary composites and processes suitable for use on, or with, the present composites, systems, and methods. Thus, the incorporated subject matter shall not serve to limit the scope of the present disclosure. It should be noted that while these prior patent publications provide some discussion on making elastic composites and then incorporating the same into absorbent articles, the present disclosure is, in at least one respect, more particularly directed to providing an improved system and method of making an elasticized absorbent article and/or a web of elastic composite bodies. More specifically, one directive of the present disclosure is to provide a method and system, whereby and wherein the elastic composite and its formation are seamlessly integrated into the method of making the article and into the elasticized article itself.

One key feature in the performance of successful absorbent article, such as baby diapers and pants and adult incontinence products, is the ability to contain urine and feces, and the ability to prevent such material from escaping out of the article and soiling the wearer's cloths or bedding. Diaper and pant products may achieve this performance feature by optimizing the fit of the product around the leg, and by elasticising parts of the product around the leg to maintain a good seal. Further, an additional leg cuff or barrier may be installed on the product to further prevent any leakage.

BRIEF SUMMARY

In one aspect of the present disclosure relates to an absorbent article. The article includes a multilayer bodyside chassis (also referred to herein as an inner elasticated construction). The multilayer bodyside chassis has an inner elastic construction (e.g., elastic distributions 2110) sandwiched between a first fabric layer and second fabric layer (e.g., inner sheet and inner support sheet). The article includes a multilayer outer chassis (also referred to herein as an outer elasticated construction) having an outer elastic construction (e.g., elastic distributions 2111). An absorbent member is positioned between the multilayer bodyside chassis and the multilayer outer chassis. The inner elastic construction is supported within the first and second fabric layers to form an annular cuff (e.g., cuff 2001) projected above the absorbent member.

Another aspect of the present disclosure relates to an absorbent article. The article includes an inner elasticized chassis. An opening is formed through the inner elasticised construction. The article includes an outer elasticized chassis partially bonded to the inner elasticized chassis. The opening is coincident with portions of the outer elasticized chassis that are not bonded to the inner elasticized chassis. An absorbent member is positioned between the inner elasticised chassis and the outer elasticized chassis. The inner elasticized chassis forms an annular cuff positioned above the absorbent member. The inside circumferential edge (edge 2166 as shown in FIG. 20B) of the annular cuff defines the opening. The annular cuff may be an elasticized annular cuff, in that elastic strands are incorporated into and form a part of the annular cuff.

Another aspect of the present disclosure relates to a method of forming an absorbent article. The method includes partially bonding a multilayer bodyside chassis having an inner elastic construction with a multilayer outer chassis having an outer elastic construction, and positioning an absorbent member between the multilayer bodyside chassis and the multilayer outer chassis. The multilayer bodyside chassis forms an elasticated annular cuff projected above the absorbent member.

Another aspect of the present disclosure relates to a system to produce an absorbent article. The system includes a first form roller operatively coupled to an inner sheet web, an inner support sheet web, sets of elastic strands, an absorbent member, an outer support sheet, and outer elastic strands. The system also includes a second form roller operatively coupled to an outer sheet web and positioned to receive a product of the first form roller.

A further aspect of the present disclosure relates to an absorbent article that includes an elasticized chassis and an absorbent member supported adjacent the elasticized chassis. The absorbent member is elasticized.

Another aspect disclosed herein includes an absorbent article that includes a first multi-layered chassis, a second multi-layer chassis, and a core composite having a thickness substantially less than a lateral and longitudinal expanse. The core composite is disposed between the first and second chassis.

Another aspect of the present disclosure relates to an absorbent core that includes one or more folded core sections that are biased upwards. The upwardly biased folded core sections form one or more cuffs.

Another aspect of the present disclosure relates to a method of making a modified absorbent core. The method includes slitting an absorbent core, and folding portions of the slitted absorbent core positioned between two slits.

BRIEF DESCRIPTION OF THE DRAWINGS

So that the manner in which the features and advantages of embodiments of the present disclosure may be understood in more detail, a more particular description of the briefly summarized embodiments above may be had by reference to the embodiments which are illustrated in the appended drawings that form a part of this specification. It is to be noted, however, that the drawings illustrate only various exemplary embodiments, and are therefore not to be considered limiting of the scope of this disclosure, as it may include other effective embodiments as well.

FIG. 2A is a simplified diagram in side view of a system or apparatus for making an elastic composite or elastic composite web. The system or apparatus, or portions thereof, of FIG. 2A may be used for making one or more portions of the absorbent article shown and described with respect to FIGS. 19-24F;

FIG. 2B is a plan view of the system in FIG. 2A;

FIG. 8A is a simplified illustration in isometric view of another disposable absorbent article;

FIG. 9 is a simplified illustration of yet another elastic composite web;

FIGS. 11A-11B are simplified illustrations of an elastic composite body;

FIG. 13 is a flowchart diagram for a method of making an elasticized absorbent article. One or more of the steps shown and described with respect to FIG. 13 may be utilized to form the absorbent article shown and described with respect to FIGS. 19-23;

FIG. 14 is a flowchart diagram for a method of making an elastic composite web. One or more of the steps shown and described with respect to FIG. 14 may be utilized to form the absorbent article shown and described with respect to FIGS. 19-24F;

FIG. 20 is an exploded view showing the different layers of the absorbent article of FIG. 19;

FIG. 24A is an illustration of an absorbent member or core;

FIG. 24B is an illustration of a slitted absorbent member or core;

FIG. 24C is an illustration of a folded absorbent member or core;

FIG. 24D is an illustration of an elasticated absorbent member or core;

DETAILED DESCRIPTION

Embodiments of the present disclosure will now be described more fully with reference to the accompanying drawings, which illustrate various exemplary embodiments. The disclosed concepts may, however, be embodied in many different forms and should not be construed as being limited by the illustrated embodiments set forth herein. Rather, these embodiments are provided so that this disclosure will be thorough as well as complete and will fully convey the scope to those skilled in the art and the best and preferred modes of practicing the embodiments. For example, many of the exemplary descriptions provided herein are concerned with training pants for infants and young children. Aspects of the disclosure described may, however, be equally applicable to designs for and the manufacture of, baby diapers, adult incontinence products and other similar products.

For purposes of the present description, the terms "elastic composite", "elastic composite body", and "elasticized article" refer to a multi-layer or multi-component construction that incorporates elastomeric material(s) or elastic member(s). In this construction, a plurality of elastic members, such as threads or strands, may be connected to or disposed adjacent one or more materials, e.g., a backsheet and topsheet. In this way, the elastic members impart elasticity to the connected or adjacent layers and thus, to that part of the garment or article. Such an elastic structure may be a distinct attachable component of the garment or article, or may be a distinct portion or section of the garment body article or a larger, unitary component of the garment.

Further, as used herein, the term "web" refers to an extended, conveyable sheet or network. The term "substrate" refers to a supporting web, sheet, or layer, such as a web or layer of backsheet onto which elastics adhere or are otherwise supported. Further, a web may be of an elastic composite and/or provide a plurality or series of discrete elastic composite bodies. In some embodiments described herein, such elastic composite bodies may be separated from the web to form the basis of a disposable absorbent article such as a diaper or absorbent pants.

FIGS. 1A-18 depict articles and portions or aspects thereof, systems for making the same, and processes for making the same, as shown and described in U.S. patent Ser. No. 13/200,100, now issued as U.S. Pat. No. 9,205,003, the entirety of which is incorporated herein by reference. In some embodiments, one or more of the systems and processes, or portions thereof, described with respect to FIGS. 1A-18 may be applied for production of the absorbent article described with respect to FIGS. 19-24F. In some embodiments, one or more portions or aspects of the articles described with respect to FIGS. 1A-18 may be combined with one or more portions or aspects of the articles described with respect to FIGS. 19-24F.

Article with Elastic Distributions

Figure 1A:
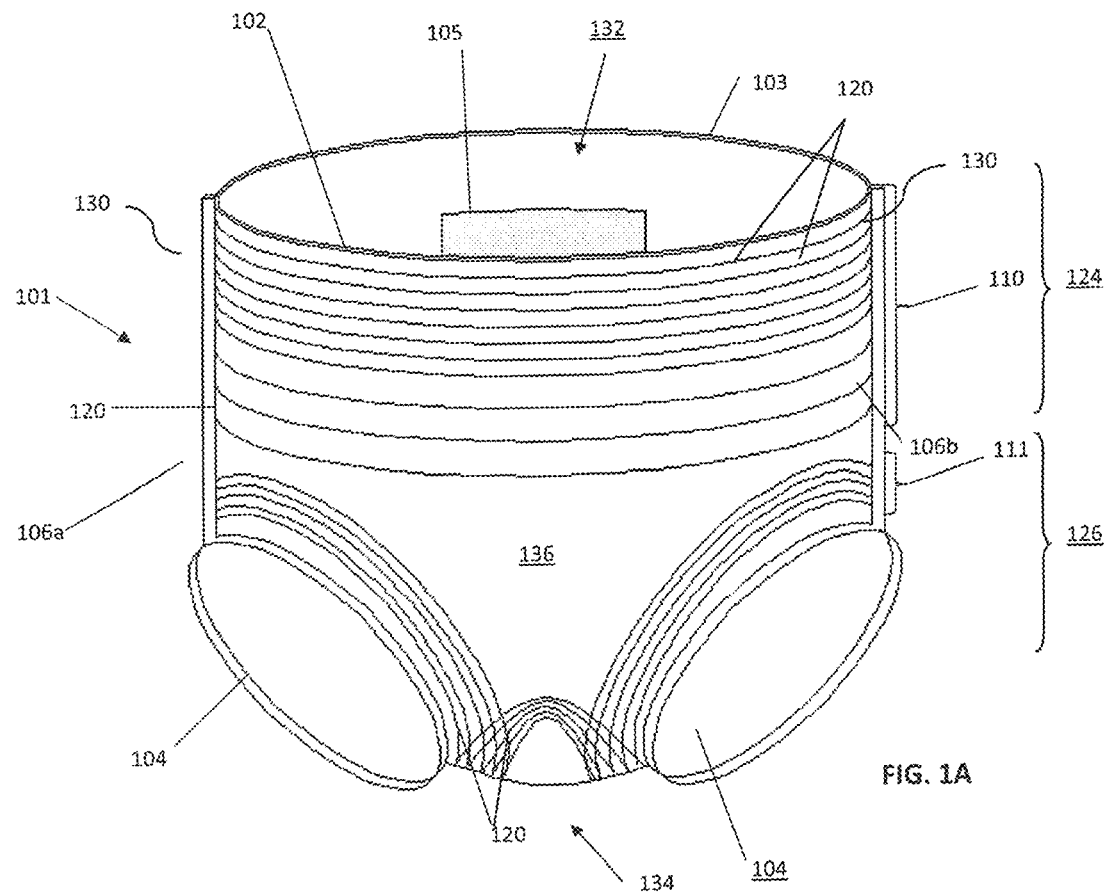
FIG. 1A is a simplified illustration in isometric view of a disposable absorbent article.

FIG. 1A illustrates a first embodiment of the present disclosure, in the form of disposable absorbent training pants 101. The upright absorbent pants 101 are formed from an elasticized composite body 136 with a first or front half portion rotated about a symmetrical line to join a substantially identical second or rear half portion. The two half portions are joined at a pair of sealed side seams 130. Each side seam 130 consists of a first or bottom segment of a side edge 106 joined to a second or top segment of the same side edge 106 (as will be further explained below). The resultant absorbent pants 101 has a front longitudinal waist edge 102, a rear longitudinal waist edge 103, and the pair of sealed side seams or seals 130 each on a lateral side of the absorbent pants 101. To facilitate the present description of the disclosure, the pants body 136 is sometimes described as having an upper waist region 124 and a lower waist, leg, and crotch region (lower region 126). The absorbent pants configuration 101 is also provided with a fluid distribution and storage construction or absorbent core 105 on the inside of the pants 101 and about a crotch region 134. In one aspect of the disclosure, the forming of the two lateral side seals 130 immediately creates the absorbent pants configuration 101. This absorbent pants configuration 101 includes a waist opening 132 defined by the joining of the two waist edges 102 and 103 to complete a continuously encircling waist edge. The pant configuration 101 further includes two leg openings 104 formed by the joining of the half portions (as will also be further explained below).

The side seams 130 may be provided by a permanently bonded seal or a refastenable seal. A permanent side seal may be achieved, for example, through the use of adhesive bonding, thermal bonding, ultrasonic bonding or any other suitable bonding mechanism. A refastenable side seal may be achieved through the use of adhesives, hook and loop materials or other refastenable mechanisms.

To enhance the comfort and fit of the absorbent article, as well as its capacity to contain fluid and minimize the occurrence of leakage of fluid through the waist and leg openings 132, 104, the disposable absorbent article 101 is provided with strategically-placed elastomeric materials 120. In an embodiment, these elastomeric materials consist of strands or yarns of elastic thread such as natural rubber, latex strands or synthetic elastomers such as Lycra or Spandex yarns. Other suitable elastomeric materials include, but are not limited to, stretchable elastomeric films, elastomeric ribbons, elastomeric nonwovens and elastomeric adhesives. For purposes of this description, any discussion of the elastomeric materials will be confined to the use of elastomeric strands or yarns, which may be referred to as elastic strands or elastics. It will become apparent, however, that these elastomeric materials may be readily substituted with many other types of elastomeric material.

The absorbent pants 101 in FIG. 1A incorporate multiple distributions of elastic strands 120 in the upper waist region 124 and in the lower waist, leg and crotch regions (lower region 126). These distributions of elastic strands render the composite body 136 with strategically localized and advantageously configured elasticity. Upon sealing of the side edges 106, this feature translates directly and readily to the resultant absorbent pants 101 and ultimately, to the pants 101 as worn by the user. Accordingly, the pants 101 of the disclosure may be referred to as an elasticized disposable absorbent article 101. To elaborate, each of the elastic distributions in the absorbent pants 101 define a substantially annular area or region of elastics or elasticity. In the upper waist region 124, a set or distribution 110 of the elastic strands 120 is arranged generally circumferentially about the waist opening 132 and just below the joined waist edges 102, 103, and thus, encircles the waist of the user. In some aspects, the elastic strands 120 are mutually spaced apart and generally parallel with the waist edges 102, 103. Accordingly, the absorbent pants 101 may be equipped with a particularly advantageous annular region of elastic and elasticity snugly encircling the entire waist of the user and, acting therewith, to effectively seal the waist opening 132. In the lower region 126, multiple distributions of elastic strands 120 extend substantially completely about the leg openings 104 and the crotch region 134. One set or distribution 111 of elastic strands 120 encircle the leg opening 104 and forms an elasticized annular area or region thereabout. A third annular area or region of elastics is generally positioned centrally in the crotch region 134.

The elastic annular regions about the waist opening and the leg openings are advantageously maintained substantially all the way around the sealing subject (i.e., the potential opening between the waist and the waist edge 102,103 and the potential openings between the thigh and the circular side edge of the article 101). Moreover, the strength and direction of the elastic forces are maintained generally uniform about the openings. A more effective and more reliable seal is achieved because all potential leakage points around the opening are addressed. Uniformity in the elasticity about the waist or thigh also helps to prevent uneven fit, which can lead to a poor seal. Notably, the elastic distributions 110, 111 in the composite body 136 extend substantially all the way from one side edge to the opposite side edge (as explained below) and, upon formation of the pants configuration 101, extend substantially continuously (without ends) about the article 101. It should be understood, however, that the elastics of the annular regions do not necessarily have to touch or overlap. It is sufficient for the ends of elastics to be proximate to opposing ends so as to effect generally uniform elasticity about the sealing subject or edge, substantially similar to an actual ring of elastic placed therebout.

It should be noted that the elastic strands 120 about the leg opening 104 may overlap into the crotch region 134. It should also be noted that the elastic strands 120 in the upper and lower regions 124, 126 are not necessarily mutually exclusive and elastic strands in one region may overlap and intersect elastic strands in the other region.

Figure 1B:
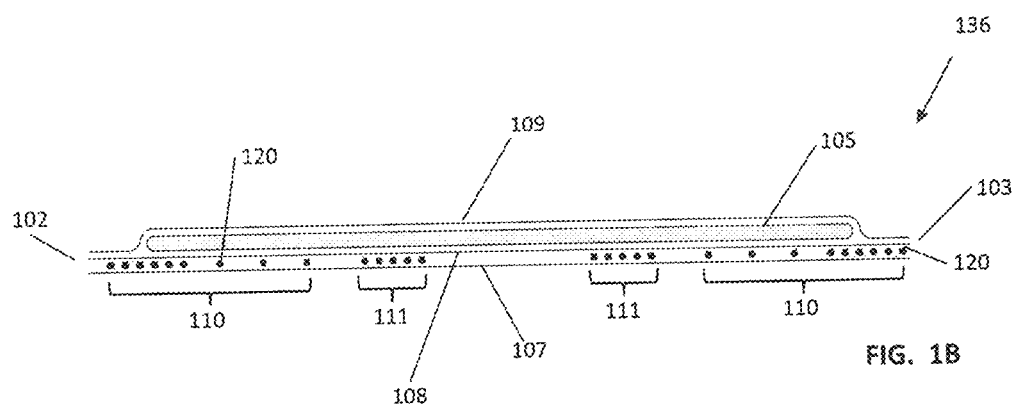
FIG. 1B is a cross-sectional view an elastic composite or elastic composite web.

In one aspect of the present disclosure, the disposable absorbent article 101 having one or more annular regions of elastics or elasticity may be made utilizing a single, unitary elastic composite body 136 (or prior to making the pants configuration 101, simply elastic composite 136). FIG. 1B is a cross-sectional view of an exemplary elastic composite 136 specifically for the absorbent pants 101 of FIG. 1A. Among other things, this view describes the multiple distributions of the elastic strands 120 in the elastic composite 136 utilized in the absorbent pants 101 according to the present disclosure. The elastic composite 136 has a first or bottom edge 102 and a second or top edge 103 (which ultimately define the waist edges 102, 103 in the pants configuration 101). The composite 136 also has an outer, fluid impermeable backsheet layer 107, an optional intermediate layer 108, a fluid distribution and storage construction or core 105 and a fluid permeable topsheet 109. The fluid impermeable backsheet layer 107 may be selected from a range of materials that include hydrophobic, fluid impermeable nonwoven materials, breathable and non-breathable polyethylene films or laminates of these materials. The optional intermediate sheet layer 108 may also include hydrophobic, fluid impermeable nonwoven materials, breathable and non-breathable polyethylene films, and laminates of said materials or other suitable materials. As shown in FIG. 1B, the two sheet layers 107, 108 help retain the elastic distributions 110, 111 in place, although, in some embodiments, the elastic distributions are adhered only to the surface of the backsheet layer 107. The fluid distribution and storage construction or absorbent core 105 may be composed of nonwoven materials, aperture films, tissue, cellulose fluff pulp, superabsorbent polymer particles or fibres or any other materials that can be utilized to distribute and absorb the fluid and solid insults passed into the article when it is used. Furthermore, fluid permeable topsheet 109 may comprise a hydrophilic, fluid permeable nonwoven web or an apertured material.

For the absorbent pants 101 of FIG. 1A, the exemplary elastic composite 136 reveals a first distribution 110 of elastic strands 120 directed along each of the first edge 102 and the second edge 103. In this embodiment, a grouping of six spaced apart strands 120 is generally bunched together along the edges 102, 103, while three individual strands 120 are located inwardly of these strands 120. The spacing between the three individual strands 120 is wider than that of the first six strands 120. This spacing of strands 102, 103 corresponds with the spacing of the strands 120 in the upper region 124 of the disposable absorbent article 101 of FIG. 1A, which concentrates elasticity near the edges 102, 103. The elastic composite 136 also features the two other distributions 111 of elastic strands 120. Two distributions 111 of five strands 120 each are located inwardly from the two outside distributions 110, as shown in FIG. 1B. As will be further described below, these two distributions 111 correspond with the elastic distributions 111 about leg openings 104 and in the crotch region 134 of the disposable absorbent article 101.

Figure 3:
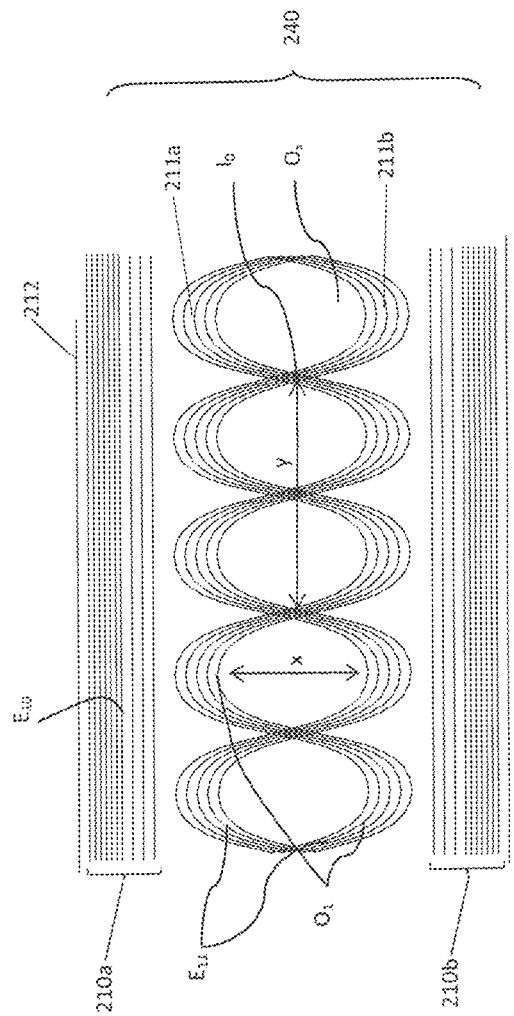
FIG. 3 is a simplified illustration of an elastic composite web.
Figure 4:
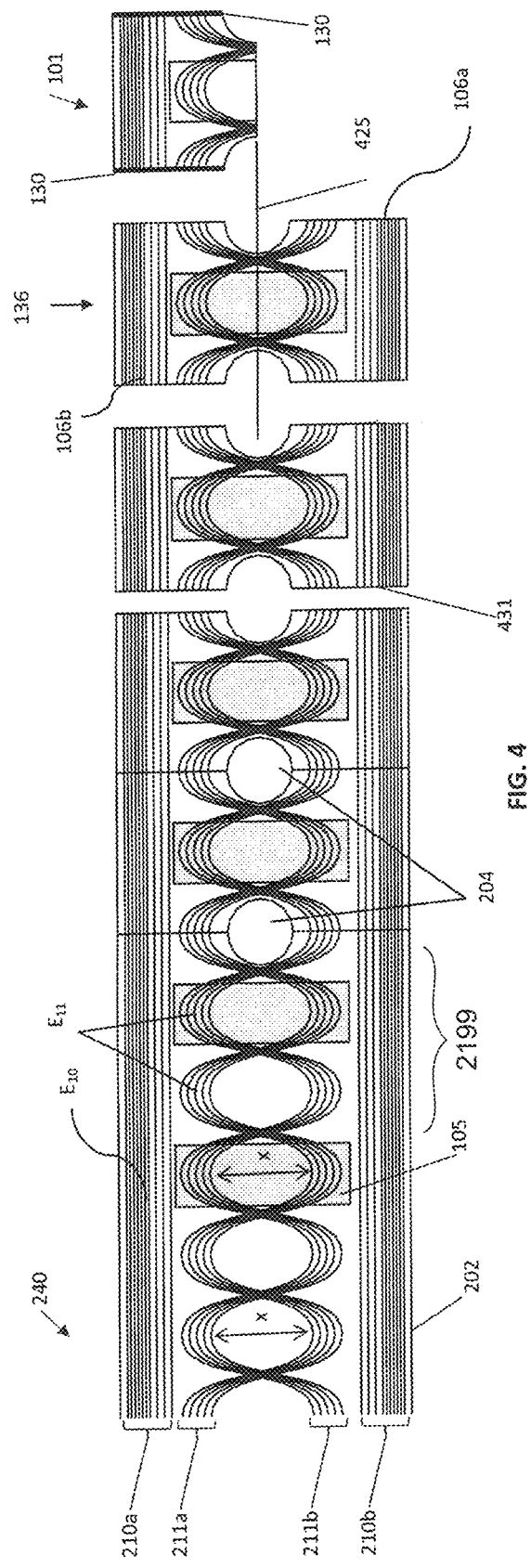
FIG. 4 is a simplified illustration of a web-based process for making the disposable absorbent article in FIG. 1. One or more aspects of the process shown and described with respect to FIG. 4 may be utilized to form the absorbent article shown and described with respect to FIGS. 19-24F.

The simplified illustrations of FIGS. 2A and 2B describe a system 250 and method for making a web 240 of the elastic composite 136. More specifically, the system 250 and method are utilized for incorporating the desired elastic distributions 110, 111 described above in an elastic composite 136 and in a composite web 240 (and ultimately, in an absorbent article 101), according to the disclosure. The illustrated method provides an initial sub-process in making the elastic composite 136 and the disposable absorbent article 101 in FIGS. 1A and 1B. FIG. 4 illustrates the subsequent and remaining stages in this method. Both FIGS. 3 and 4 depict a unitary elastic composite web 240 that is particularly suited for making disposable absorbent articles 101. As will be described, the composite web 240 can contain and present four continuous, machine-directioned distributions of elastic strands that trace a specific, advantageous pattern. At least two of the distributions are described by a periodic function featuring a trough and a summit. The other two distributions may be maintained along a direct path.

Referring now to FIGS. 2A and 2B, the system 250 and method convey, append, and manipulate an elastic composite web 240 in a substantially linear process and in the machine direction. For purposes of description, the web 240 is referred to as having a first or bottom edge 202, a second or top edge 203 spaced apart from the first edge 202 in the cross-machine direction and generally parallel therewith, a cross-machine width defined between the two edges 202, 203, and a longitudinal centerline YY. In some descriptions, the cross-machine direction across the web 240 and components supporting the web 240 may be referred to as a lateral direction, while the machine direction may be described as corresponding to a longitudinal direction. In some aspects, the elastic composite web 240 is advanced at a uniform rate of speed in the longitudinal or machine direction.

In an embodiment, the method initially uses the separate, continuous conveyance of each of six elements of the elastic composite 136 to a joining mechanism such as a nip roller 218 (see e.g., FIG. 2A). These elements include a first material sheet 212, a second material sheet 213, a first set 210a of pre-tensioned elastic strands along the top edge 203, and a second set 210b of pre-tensioned elastic strands along the bottom edge 202. The first and second sets 210a, 210b of elastics strands are aligned in mutually parallel alignment but spaced apart specifically according to a pre-determined arrangement. In this specific embodiment, the first and second sets 210a, 210b are mirror images of one another. Additionally, two other sets 211a, 211b of pre-tensioned elastic strands are conveyed along a machine direction laterally inwardly of the first and second sets 210a, 210b of pre-tensioned elastic strands. As best shown by FIG. 2A, both the first and second sets 210, 211 of elastics may be introduced and conveyed toward the nip roller 218 along the horizontal plane of the web 240. The two inwardly sets 211a, 211b of elastics are also introduced on the same web plane. The two material webs 212, 213, may on the other hand, be initiated from generally above and below the web plane, respectively (hence, sometimes referred to as upper and lower material webs or sheets).

The elastic strands may be received in a tensioned state by means of any suitable feeding and tensioning device positioned upstream of this process (not shown). The initial lateral positions of the elastic strands, as well as the spacing between adjacent elastic strands, may be initially fixed by elastic guides 215. These fixed elastic guides 215 are mounted on two rods 219, as shown in FIGS. 2A and 2B. The elastic guides 215 typically comprise rollers, eyelets or any other suitable means for conveying and guiding the pre-tensioned elastic strands. A second set of elastic guides 216a, 216b are mounted on movable rods 221 downstream of the fixed rods 219. Each of these two movable elastic guides 216a, 216b engages one of the two inward sets 211a, 211b of elastic strands. In some aspects, the movable rods 221 and movable guides 216a, 216b are positioned above and below the web plane, respectively. Thus, while a first set 211a of elastics is introduced along the web plane, it is directed slightly above the web plane a short distance after introduction. Similarly, the other set 211b is directed slightly below the web plane after introduction. This adjustment occurs before the two sets 211a, 211b of elastics are engaged by conveying means 217 and advanced to the nip roller 218.

It should be noted that the specific components of the system 250 shown in the Figures may be substituted with other suitable means or components. For example, in alternative systems, stationary guides or eyelets may be mounted on a fixed frame. Further, the movable guides may be mounted or associated with mechanical arms, cam systems, and other suitable mechanisms.

The sets 210a, 210b of elastic strands are distributed in a generally parallel alignment toward the nip roller 218. These elastic strands are analogous with the distribution 110 of elastic strands present in the upper waist region 124 of the absorbent article 101 in FIG. 1A and are distributed in parallel relationship with the top and bottom edges 202, 203 composite web 240. For the absorbent pants 101 of FIG. 1A, the arrangement of the sets 210a, 210b of elastic strands may be identical. Other article designs may be provided, however, wherein the arrangements are not identical and one set may include more elastic strands than the other set. Also, the spacing and concentration of the elastics may, in other designs, differ to achieve a specific function or aesthetic attribute. Although such designs may deviate from the preferred arrangements for annular elastic regions, as described above, it is expected that such alternate designs will not deviate completely and that some aspects of the preferred designs will be retained (in accordance with the disclosure).

The moveable elastic guides 216a, 216b are configured to move in a direction orthogonal to the machine direction of the web 240 and serve to change and direct the placement of the sets 211a, 211b of elastic strands into the nip roller 218 and adjust the lateral spacing of the elastic strands. Accordingly, the two inward sets 211a, 211b of elastics may be referred to as variable (as opposed to "fixed") sets of elastics. By vertically spacing the two variable sets 211a, 211b of elastics (as described above), the two sets 211a, 211b can move laterally without interference from the other. In this embodiment, for example, the two sets 211a, 211b of elastics laterally cross so that a bottom set of elastics arrives at the nip roller 218 as the top side set while the other set becomes the bottom side set.

In an embodiment, the elastic guides 216a and 216b are mounted on a reciprocating mechanism such that the elastic guides are continually reciprocating in a lateral direction (orthogonal or transverse to the machine direction of the process). The guides 216a, 216b may be carried on the same continuous belt or track and move together at all times. In other embodiments, the guides 216a, 216b may be driven independently of one another, particularly if the pattern of on elastic distribution is greatly independent of the other. Suitable driving mechanisms can include a cam based mechanism, a servo driven mechanism or a hydraulic mechanism. In some aspects, the motion of the elastic guides 216a and 216b is described by a periodic function, in which a relative displacement of the elastic (or elastic guide) is a function of time (or a length of the web) plus a discrete increment (P, period). This displacement function expresses the periodic shape or pattern of the distributed elastics.

Figure 2C:
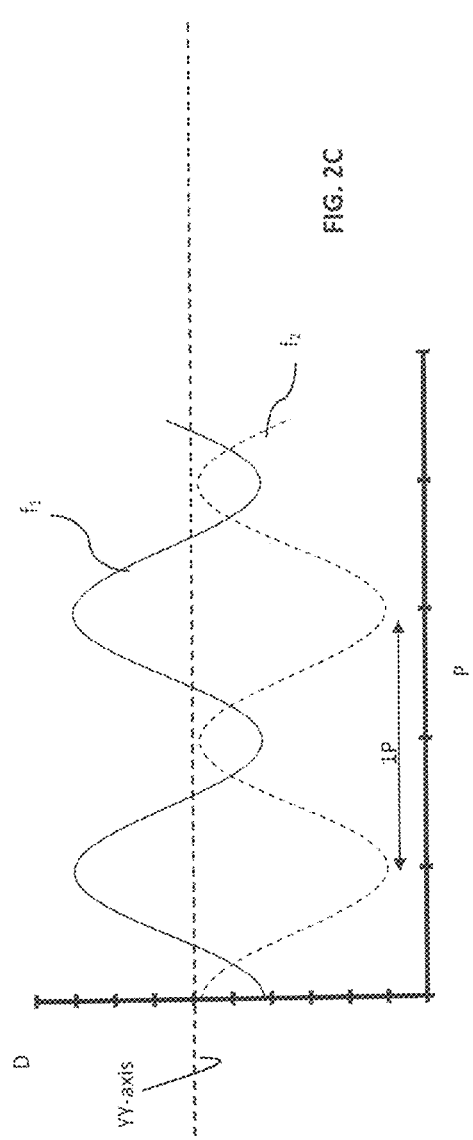
FIG. 2C is a graphical diagram of an exemplary periodic function reflecting directive lateral motion by elastic guides in FIGS. 2A-2B to produce a dual elastic distribution pattern on an elastic composite web.

The graphical illustration of FIG. 2C describes an exemplary periodic function reflecting the lateral displacement (D) of the movable guides 216a, 216b over a period of time (P) (which is proportional to the width of the elastic composite 136 relative to machine speed). The two separate functions f1, f2 show the relative lateral movement of the guides used to produce the dual elastic distribution patterns on the web. As shown by the graph, the two elastic guides cross twice during each period. The multiple crossings translate to the generation of a series of elastic annular regions on the composite web, or at least two annular regions per period (P) or elastic composite body 136.

The upper and lower sheets 212, 213 are also directed by conveyance means 217 toward the web plane and then to nip roller 218. Thus, the two sheets 212, 213 and the four sets 210, 211 of elastics arrive substantially together at the nip roller 218. The upper and lower sheets 212, 213 serve to sandwich, entrap and hold the elastic strands in position after passing through the nip roller 218. The resultant web 240 of elastic material and material webs is secured using any suitable bonding means which include, adhesive, ultrasonic or thermal bonding (not shown). In the case of adhesive bonding, the adhesive could be applied to the upper and lower sheets 212, 213 or applied directly to the sets 210, 211 of elastic strands at any point prior to the elastic strands and upper and lower sheets meeting and combining at the nip roller 218.

FIG. 3 illustrates the continuation of the system 250 and method of making the disposable absorbent article 101 illustrated by FIGS. 2A, 2B. The system 250 and method of FIGS. 2A and 2B output an elastic composite web 240 that includes an upper sheet 212, a lower sheet not shown, but directly underlying the upper sheet 212, and distributions E10, E11 of elastic strands across the cross-machine direction width of the web 240. The two variable distributions E11 of elastic strands disposed in the middle are directed by means of the periodic, lateral motion of the elastic guides 216a. 216b in FIGS. 2A, 2B (and its periodic function), which in this example, results in a sinusoidal pattern. The pattern may also be described as a series of annular elastic regions $O_1$ or areas formed by the troughs and valleys of the two variable distributions E11 of elastics. This process may produce other linear and non-sinusoidal patterns; but, for the purposes of this exemplary description, the sinusoidal pattern is employed. One set 211a of elastics is distributed in a first sinusoidal pattern E11 and are overlapped with the elastics of the second set 211b, which are distributed in a second sinusoidal pattern E11. In this example, the first and second sinusoidal patterns are mirror images of each other. The two distributions E11 also define a region $I_0$ at which one set overlaps and intersects the other. The degree to which the elastic strand patterns overlap can be measured and is, hereafter, described as the variable "X". The wavelength of the sinusoidal pattern can also be measured and is hereafter recorded as the variable "Y". Both variables "X" and "Y" are process parameters that may be adjusted by changing various process parameters such as machine speed, reciprocation speed and reciprocation depth.

FIG. 4 illustrates a process or conversion step for further modifying and then converting the elastic composite web 240 of FIGS. 2A, 2B, and 3 into the disposable absorbent article 101 in FIG. 1A. As shown in FIG. 4, the sub-process proceeds downstream from left to right whereby the initial step may be described as receiving an output (the elastic composite web 240) from the system 250 and sub-process of FIGS. 2A and 2B. A fluid distribution and storage construction or core 105 is applied centrally over one of the overlap regions Ox of the two sets 211a, 211b of sinusoidal elastic strands. The elongated core 105 is applied and positioned laterally with the length of the core 105 being deposited on the web 240 in the cross-machine direction. In this embodiment, the core 105 is situated between the upper and lower distributions E11 of elastics. Simultaneous with or immediately after the application of the core 105, a material sheet (not shown) is applied over the core 105 and the web 240. This material sheet becomes the topsheet in the disposable absorbent article 101. Additional features such as free-standing elasticised leg cuffs, fastening tapes and disposal tapes may be added to the construction at this stage.

In a subsequent step or stage in the process, circular holes 204 may be punched or cut in the web 240. In this embodiment, the holes 204 are punched centrally inside of the elastic annular regions $O_1$, but on the overlap region Ox. As shown in FIG. 4, the holes 204 are also in longitudinal alignment with the intersections $I_0$ of the elastic strands and with the wavelength distance "Y" of the sinusoidal patterns. The cutting of the holes 204 leads to the provision of the leg openings 104 in the disposable absorbent article 101. It is, therefore, in some embodiments, an important requirement of the disposable absorbent article 101 that the wavelength "Y" of the sinusoidal pattern is equal to the width of the finished article 101.

The next step in the production process entails cutting or severing the continuous composite web 240 across the cross-machine direction width and along cutting lines 431. This end cut can be accomplished by a number of mechanisms known to those skilled in the art, including a die cutting process or a water-jet cutting process. The position of the end cut is determined relative to the wavelength "Y" of the sinusoidal pattern. Notably, cutting lines 431 bisect each hole 204 and alternating elastic annular regions $O_1$. The cutting lines 431 are also spaced on either side of the core 105.

Upon separation, discrete, individual elastic composites 136 are formed. The elastic composite 136 now has a longitudinal (lengthwise) centerline that bisects the elongated core 105. Further, the composite 136 has two lateral side edges 106a, 106b along the original cutting lines. The side edges 106a, 106b consists of a top segment and a bottom linear segment. The non-linear cut-out section is positioned intermediate the two segments and is intended to form the leg openings. The elastic composite 136 also feature half elastic annular regions extending to each side edge 106a, 106b, which were severed by the cutting lines, and complete annular elastic annular regions in the center. The elastic composite 136 also has a core 105 situated centrally over the central elastic annular region.

Finally, the elastic composite 136 is folded along fold line 425, which corresponds to the longitudinal axis YY of the web 140. The elastic composite 136 in this embodiment is symmetric about this axis YY. Accordingly, when folded, each feature or portion on the bottom half match and cover the exact same feature or portion on the top half. The result is the disposable absorbent article 101 in FIG. 4 (and FIG. 1A). In the flat and folded state, the article 101 now displays a quarter of each leg 104 hole and a quarter of each half-annular region on the side edges 106a, 106b. To finalize the absorbent pants construction, the matching side edges 106a, 106b are sealed (seals 130), while the matching upper-lower edges 102, 103 and the quarter-leg holes are not. The specific manufacturing process for this embodiment employed a high "X" value.

Figure 5:
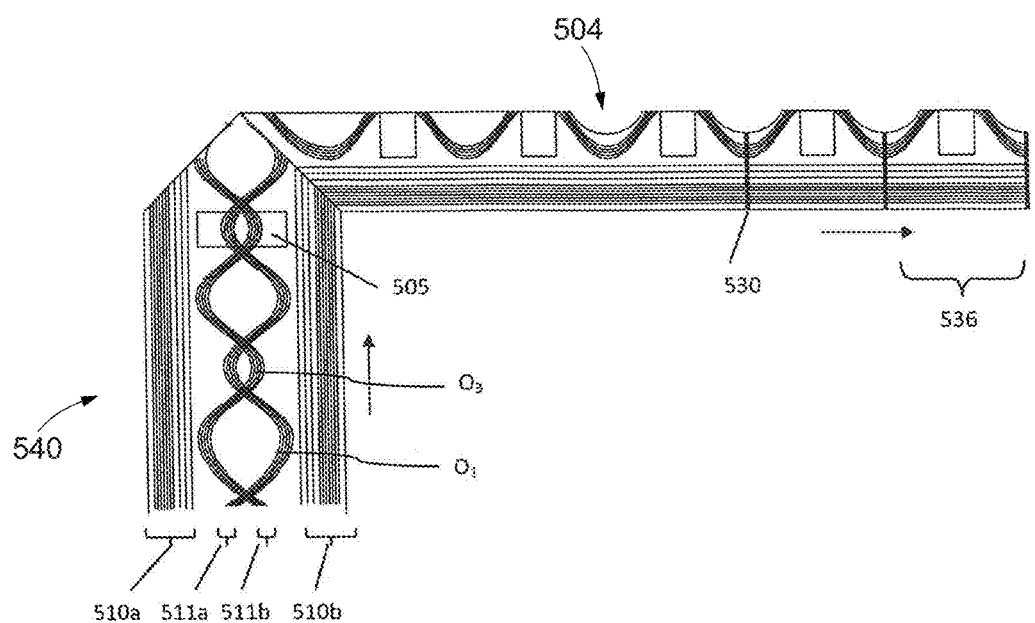
FIG. 5 is a simplified illustration of a web-based process for making a disposable absorbent article. One or more aspects of the process shown and described with respect to FIG. 5 may be utilized to form the absorbent article shown and described with respect to FIGS. 19-23.

The process described with reference to FIGS. 2-4 is one example of the process of making the absorbent article. It is not required that the steps described are completed in the order described. It is possible, and may in some circumstances be preferred, that the steps are completed in a different order or that some of the steps may be completed simultaneously FIG. 5 is a simplified representation and schematic illustrating a web of elastic composite 540, as well as a method or process of making the elastic composite web 540 and an absorbent article, all according to an alternate embodiment of the disclosure. The illustration provides the latter or downstream stages of the process, after introduction and application of sets 510a, 511A, 511b, 510b of elastics. Downstream of the nip roller (not shown), the elastic composite web 540 generally consists of two or three layers of sheet material and the desired elastic patterns and elastic annular distributions for the waist region and the crotch region. In this embodiment, the two variable distributions 511a, 511b of elastics trace a pattern and period that consists of a large (wide) elastic annular region $O_1$ and an overlap region bounded therein and a small (close) elastic annular region $O_3$ and its overlap region.

In a downstream stage, a desired absorbent core section 505 is applied onto the elastic composite web 540, over the close elastic annular region $O_3$. Then, a material sheet layer (of topsheet) is applied over the elastic composite web 540 and the core 505, to provide an enhanced elastic composite web 540 having all of the major components desired of the inventive absorbent article. At this step, the elastic composite web 540 may be described as a web of elastic composite bodies. In one aspect of this embodiment of the disclosure, the resultant elastic composite web 540 is folded about the longitudinal centerline YY. As shown in FIG. 5, this folding step may be accomplished by diverting the conveyor run about 90 degrees and such that one half of the elastic composite web 540 also rotates 180 degrees onto itself. The result is a 90 degree turn at which one half of the longitudinally extending web folds over and matches its mirror image. The folded web 540 reveals a series of one-half sections of the wide annular regions $O_3$. Using a conventional puncher or cutter, leg holes 504 (or more particularly, half of the leg holes) may be punched out of the elastic composite web 540 at a location within the wide overlap region and in between core sections 504. In this embodiment, this semi-circle cut is made at the upper edge of the folded elastic composite web 540.

Furthermore, a sealing bond or line 530 is applied from the leg hole 504 towards the side edge, thereby describing the boundaries of a unitary elastic composite body 536 according to the disclosure. In some aspects, sealing is achieved by ultrasonic bonding, thermal bonding, and the like. Finally, discrete units 536 of the elastic composite web 540 may be severed by cutting through the wide sealing or bonding line 530. In further embodiments, the sealing and cutting steps may be performed simultaneously. The result is an elastic composite web in the form of training pants, according to the disclosure.

Figure 6:
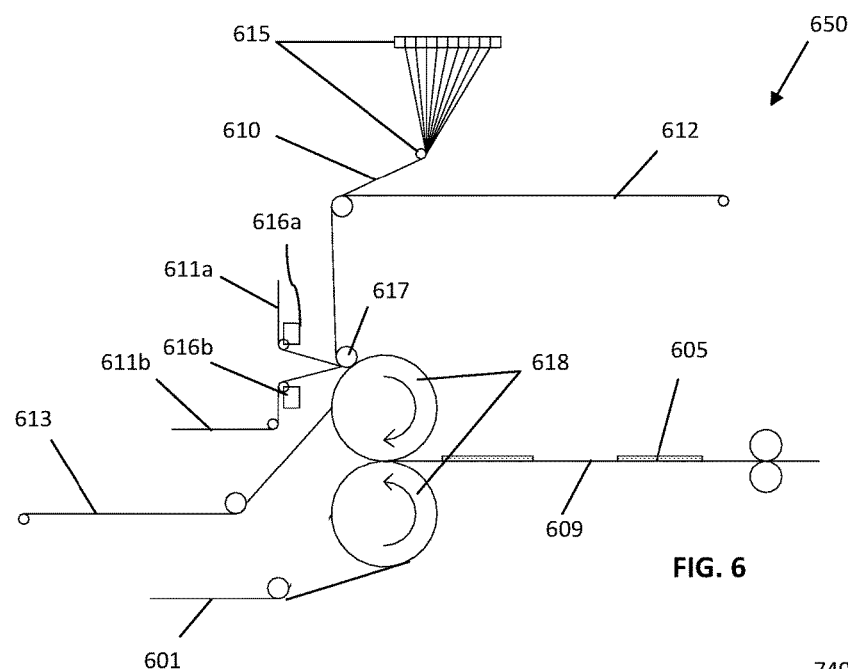
FIG. 6 is a simplified schematic of system for making the disposable absorbent article in FIG. 1. One or more portions of the system shown and described with respect to FIG. 6 may be utilized to form the absorbent article shown and described with respect to FIGS. 19-24F.

Now turning to the alternative illustration and schematic of FIG. 6, an alternative system 650 and method of making the disposable absorbent article utilizes a few different steps and sequences. A first material sheet 612 is conveyed separately by conventional means. Pre-tensioned elastics 610 (for the upper waist regions) are applied on the sheet 612, optionally near the side edges, as previously described, using elastics guide 615. The resulting elastic composite 640 is then conveyed toward and by conveying means 617. Two sets 611a, 611b of elastics are also moved and conveyed toward the conveying means 617, utilizing elastic guides 616a, 616b. As before, the elastic guides 616a. 616b vary the lateral position of the set 211a, 211b of elastics in accordance with a periodic function and to elicit a preferred pattern. Thus, the elastic composite web 640 meets the two sets 611a, 611b of variable elastics at nip roller 618, thereby enhancing the original web 640 with preferred distributions of elastics. These preferred distributions include a series of annular regions, as in earlier-described embodiments.

Furthermore, a separate combination web is applied on the elastic composite web 640 by a second nip roller 618. This subsequent application includes incorporation of a web of sheet material upon which core materials are already intermittently deposited, as shown in FIG. 6. The resulting output of the second nip roller 618 is an elastic composite web 640 having two material sheets and two sets of variable elastics and two sets of mutually parallel pre-tensioned elastics, similar to the outputs of the systems and processes of FIGS. 2A, 2B. Combination web includes a second material sheet 613 and sheet 601. Also core 605 is applied onto the resultant combination web 609.

Figure 7:
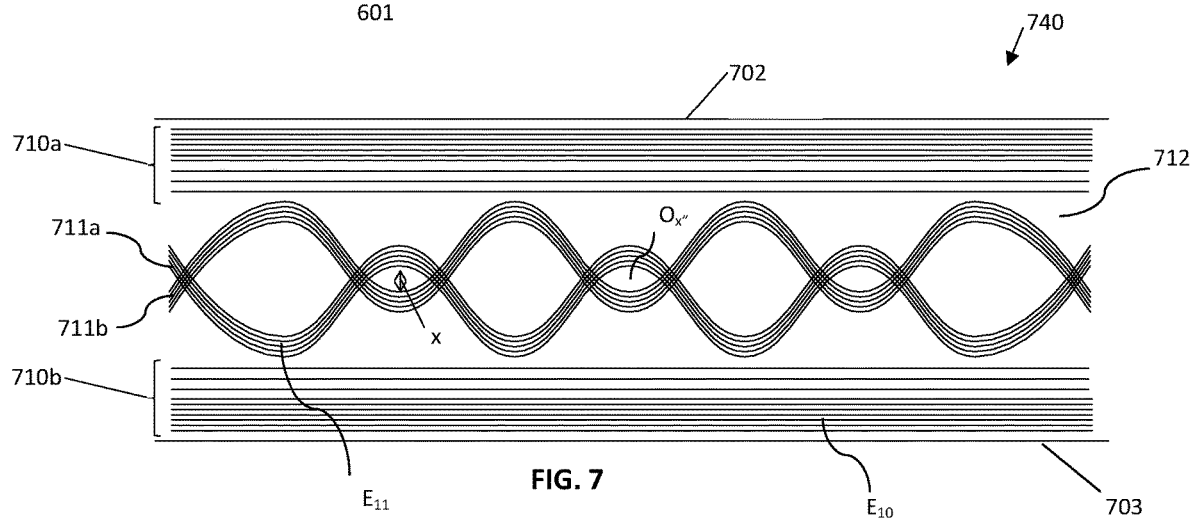
FIG. 7 is a simplified illustration of an elastic composite web employed in a web-based process for making a disposable absorbent article.
Figure 7A:
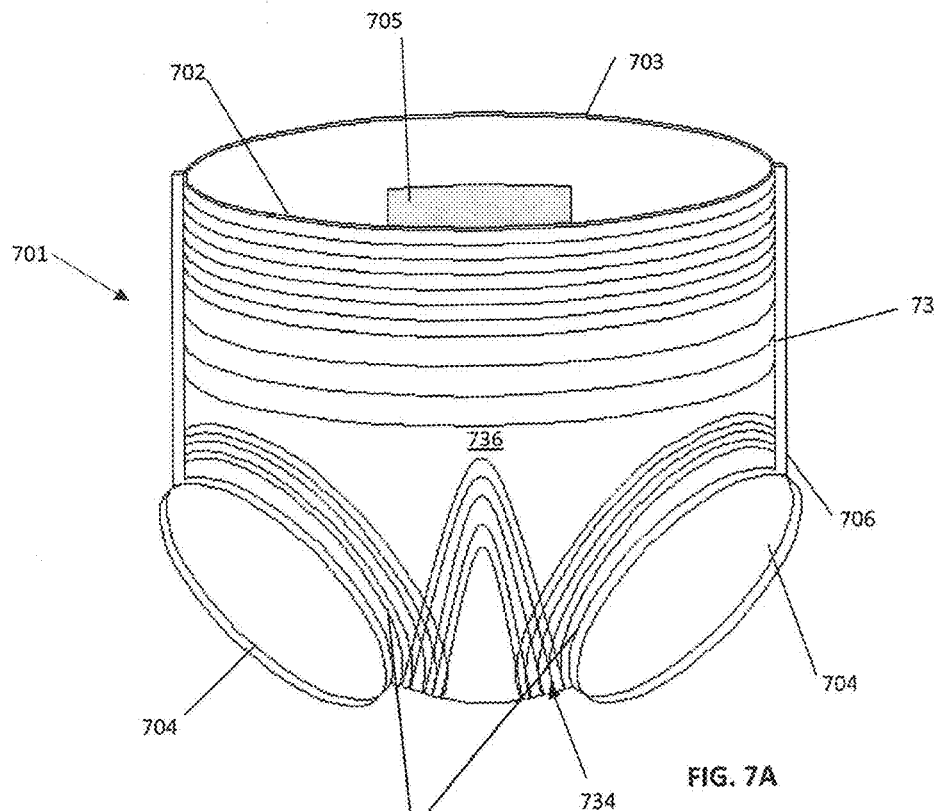
FIG. 7A is a simplified illustration in isometric view of a disposable absorbent article.
Figure 8:
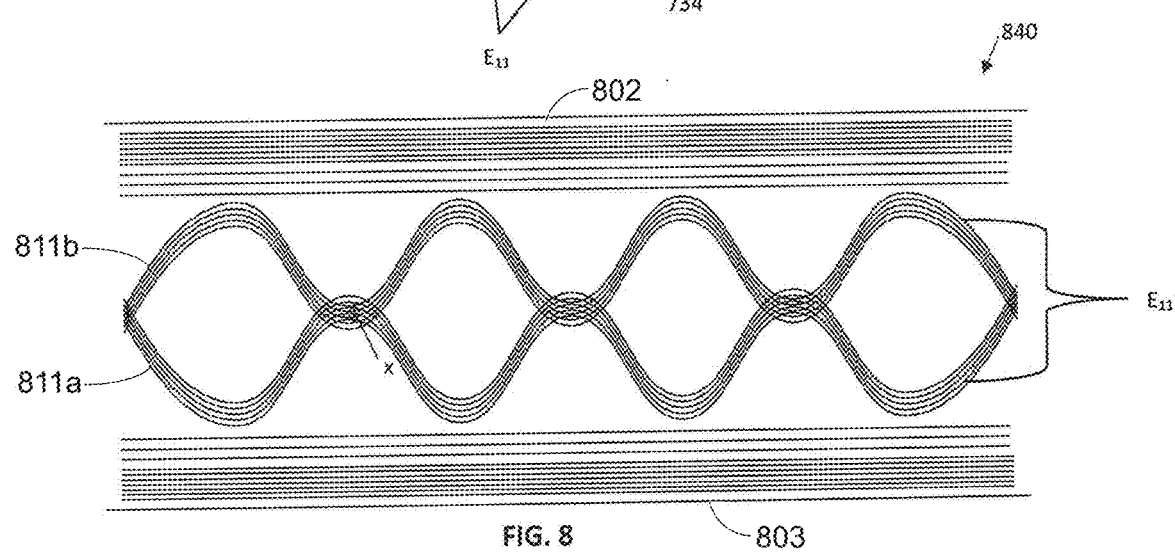
FIG. 8 is a simplified illustration of yet another elastic composite web.

FIGS. 7-9 illustrate further embodiments of the elastic composite webs and distribution that can be achieved by and/or utilized in the present disclosure, wherein like reference numerals are used to indicate like elements. Referring first to FIG. 7, the elastic composite web 740 includes an upper or backsheet material sheet 712, a lower material sheet (not shown), but directly underlying the upper sheet 712, and multiple distributions of elastic strands. Distribution of elastic strands 710a, 710b are provided along each of the upper and lower edges 702, 703 of the web 740. These distributions ultimately make up the elastic annular region about the waist opening. Between these two distributions, two distributions 711a, 711b of variable elastics are provided (for the lower waist, crotch and leg regions). As in FIG. 3, these variably positioned elastic strands are distributed by means of the periodic, lateral motion of the elastic guides in FIG. 2A, optionally to elicit a sinusoidal pattern. The first set 711a of elastics is distributed in a first sinusoidal pattern and are overlapped with the other set 711*b* of elastics distributed in a second sinusoidal pattern. In this exemplary embodiment, the first and second sinusoidal patterns are mirror images of each other. In this embodiment the degree of overlap "X" of the two elastic patterns is much smaller than that described in the embodiments relating to FIGS. 3 and 4. The resultant absorbent article made from this type of elastic distribution is described in FIG. 7, and features a greater amount of elastic material in the crotch region and less elastic material in a mid waist region. FIG. 7A depicts an absorbent article 701 having rear longitudinal waist edge 703, front longitudinal waist edge 702, core 705, linear segments 706, side seams 73, leg openings 704, elastic composite body 736, and crotch region 734.

FIG. 8 illustrates an alternate elastic composite web 840, wherein the degree of overlap or value of "X" is substantially zero or thereabout. An illustration of the absorbent article 801 utilizing this elastic distribution pattern and an elastic composite body 836 from severed from the web 840 is shown in FIG. 8A. The crotch region 834 is not as broadly elasticized as that of the absorbent article 701 in FIG. 7A. Article 801 also includes rear longitudinal waist edge 803, front longitudinal waist edge 802, core 805, linear segments 806*a*, 806*b*, side seams 830, leg openings 804, waist opening 832, and set of elastic distributions 810.

Figure 9A:
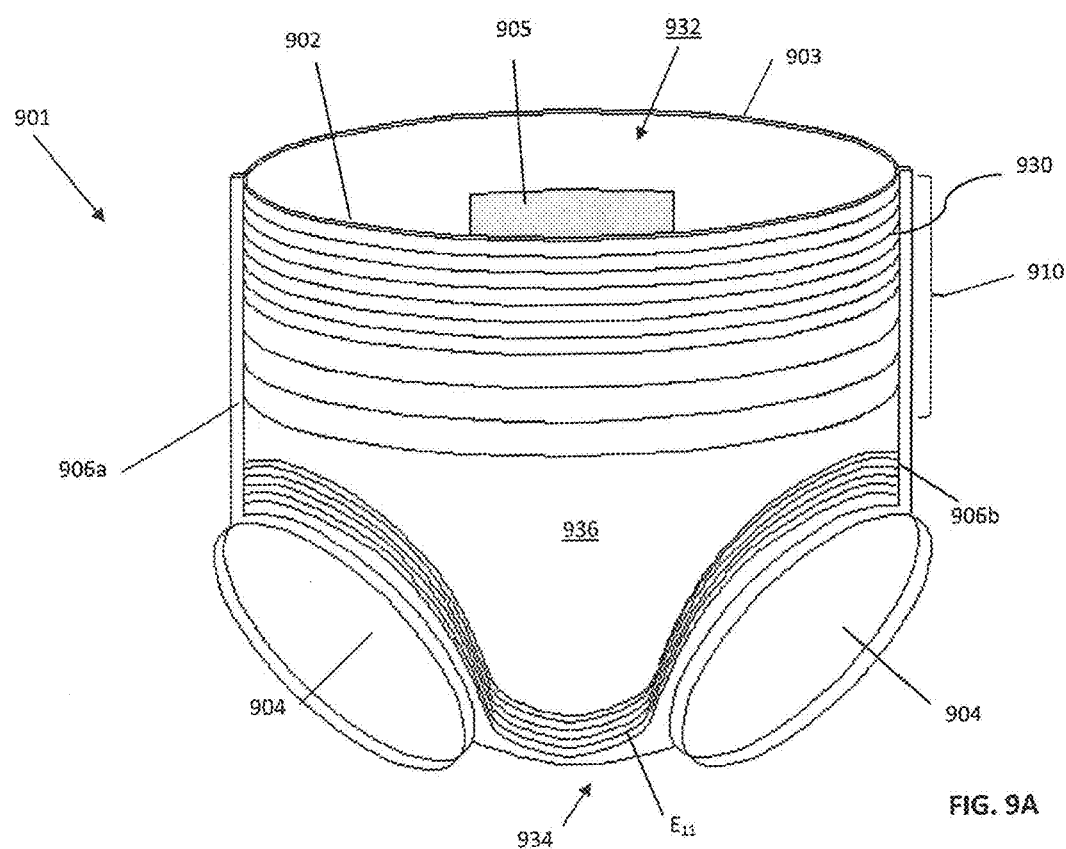
FIG. 9A is a simplified illustration in isometric view of another disposable absorbent article.

FIG. 9 illustrates yet another, further embodiment of an elastic composite web 940 according to the present disclosure. This alternate composite web 940 employs an alternate variable distribution 911*a*, 911*b* of elastics. Specifically in this embodiment, the variable set 911*a*, 911*b* of elastic strands are distributed in a pattern in which the two sets do not overlap. In this example, the value of "X" is said to be negative. Although the patterns do not provide a series of completely annular elastic regions, the value of "X" is maintained sufficiently small so as to approximate a complete annular region, i.e., a substantially annular elastic region. An illustration of the absorbent article 901 utilizing such an elastic distribution and substantially annular elastic regions is illustrated in FIG. 9A. By being substantially annular, the elastics about the waist opening 932 and leg opening 904 occupy more than 85% to 95% of the complete circle, and thus, the elasticity about the opening is practically continuous and substantially complete. Article 901 also includes rear longitudinal waist edge 903, front longitudinal waist edge 902, core 905, linear segments 906*a*, 906*b*, side seams 930, set of elastic distributions 910, body 936, and crotch region 934.

FIGS. 11A and 11B illustrate yet another elastic composite and disposable absorbent according to the present disclosure. The elastic composite is similar to that provided in FIGS. 8 and 8A. The overlap region dimension "X" has a value of zero, in that the two distributions 1111*a*, 1111*b* meet but do not completely cross. Instead, the two elastic distributions 1111*a*, 1111*b* form a broad, somewhat elongated concentration of elasticity at the center of the composite 1136. In the resulting disposable absorbent article, this feature translates to a concentration of all round elasticity in the crotch region. FIGS. 11A and 11B are also provided to show exemplary dimensions of an elastic composite of the disclosure. The Figures also show optional locations of certain element of the elastic composite 1136. For example, the core 1105 in this embodiment is located centrally over the concentration of elasticity discussed above, but is cut at a width that approximates the length of the elastic concentration discussed above.

FIGS. 11A and 11B also illustrate two stages in an alternative method of making a disposable absorbent article according to the disclosure. FIG. 11A reveals a unitary elastic composite body 1136 that could have been freshly severed from a web of elastic composite, according to the disclosure. Unlike earlier described finished elastic composites, the elastic composite 1136 has not had holes or sections cut therefrom (for later-formed leg openings). Instead, the elastic composite 1136 is folded in its full rectangular frame about longitudinal axis YY. The folded elastic composite 1136 then features quarter sections of the leg holes 1104 that may be cut or stamped out. Thereafter, the side edges 1106 may be sealed to form the leg openings of the absorbent training pants, according to the disclosure.

Figure 12A:
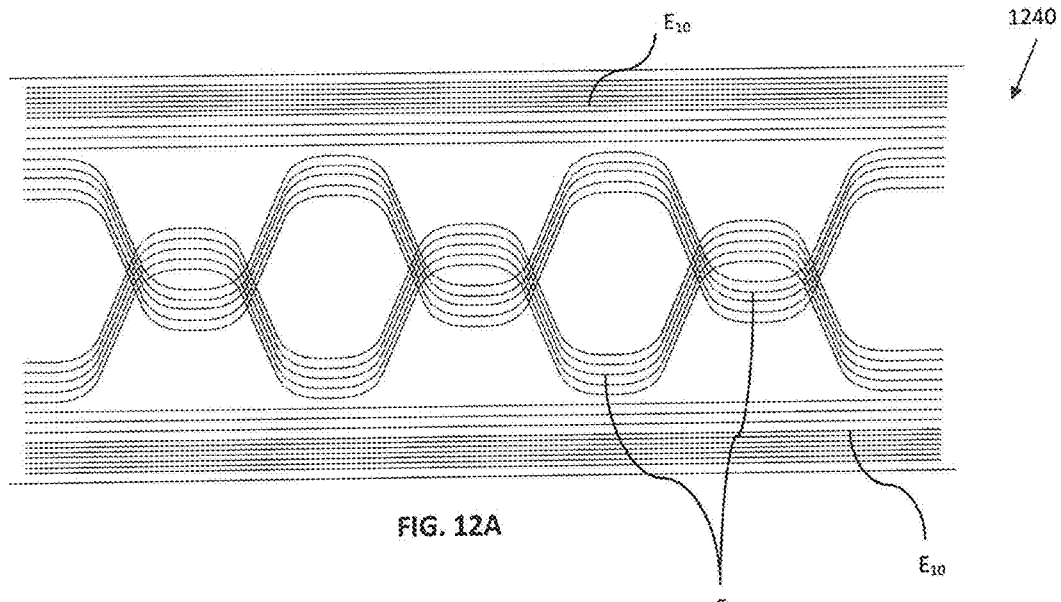
FIG. 12A is a simplified illustration of an elastic composite web having dual elastic distribution patterns applied thereon.
Figure 12B:
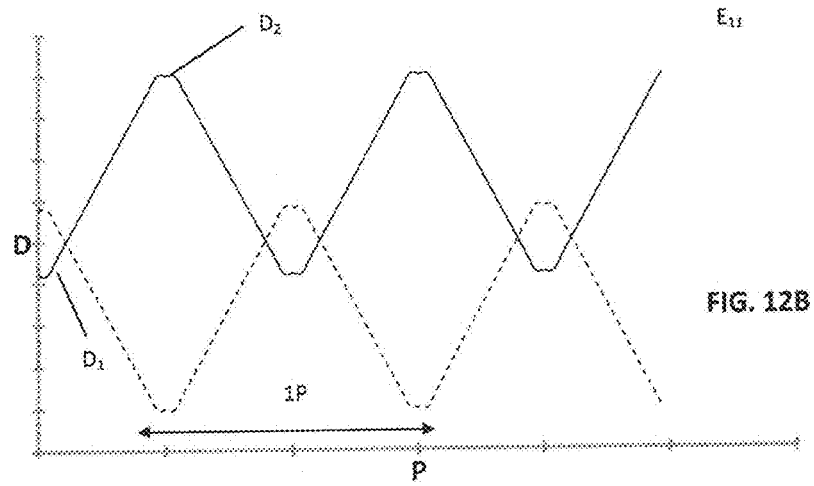
FIG. 12B is a graphical diagram of a periodic function reflecting directive lateral motion by elastic guides to produce the dual elastic distribution patterns on the elastic composite web of FIG. 12A.

In the illustration of FIG. 12A, another alternative elastic composite web 1240 is shown exhibiting a dual elastic distribution patterns (E10, E11). Among other things, the variable elastic distributions E11 feature a broader and more block-like shape to its large annular regions Ox', rather than the smoother, more rounded shape of earlier-depicted annular regions. FIG. 12B is a graphical diagram of a periodic function and pattern reflecting directive lateral motion by elastic guides to produce the variable elastic distribution patterns E11 on the elastic composite web of FIG. 12A. The graph reveals a relation characterized by a steep (almost abrupt) travel from a minimum displacement position (D1) to maximum displacement position (D2) over a half-period (½P), as well as the return to minimum displacement position (D1) over the second half-period (½P). This is reflected in the steep or abrupt angle of the elastic distribution E11 in FIG. 12A, as well as the tight concentration of the elastics during between the troughs and summits. The graph also reveals slight stall or levelling off of the elastic guide upon reaching the maximum or minimum displacement position. This feature is reflected by a somewhat flat area or plateau at each of the trough and summit of the elastics distributions E11. This pattern feature differs from the gradual, more rounded troughs or summits in earlier described elastic distribution patterns.

Accordingly, the absorbent article formed from an elastic composite of the web 1240 features a thinner, denser elastic annular region about the leg openings. Elasticity is more concentrated on the inside portion of the leg opening near and around the crotch region, as opposed to the area engaging the top of the thigh.

The flow chart 1300 of FIG. 13 illustrates an exemplary process of making the elasticized absorbent pants in FIG. 1. This process corresponds substantially with the method of making the elastic composite which as described in respect to FIG. 5. The process commences with applying multiple distributions of elastics on a moving material sheet to form a moving web of an elastic composite (step 1361). Then, each of a core section and a second material sheet is periodically applied onto the moving web to define a finished web of discrete elastic composite bodies (steps 1362, 1363). In subsequent steps, discrete absorbent pants articles are shaped from the finished web. In the shaping steps, a bottom half portion and a top half portion of the web and composite body are joined. In some aspects, the elastic composite web is folded along a longitudinal centerline (step 1364). In this specific embodiment, a section of the folded web is periodically cut-out (step 1365), thereby periodically providing cut-out sections between core sections and in between elastic distributions. Next, the two half portions are sealed along or to create two laterally extending seal lines (step 1366), thereby substantially joining multiple elastic distributions on one half portion with elastic distributions on the other half portion and creating a waist opening and pair of leg openings Finally, elasticized absorbent articles are separated from the web by severing the lateral side lines (step 1367). In some aspects, the sealing and severing steps immediately produce elastic absorbent pants having a waist opening, pair of leg openings, and multiple substantially continuous elastic distributions extending through two lateral seal lines and creating annular elastic regions about the waist opening and the leg openings.

The flow chart 1400 of FIG. 14 describes, more generally, the basic steps in a method of making an elastic composite web having multiple elastic distribution patterns thereon, according to the present disclosure. Such an elastic composite web is ultimately configured such that elastic composite bodies of absorbent pants may be separated from the web. The method commences with the step of applying multiple continuous distributions of elastics on a moving web of material sheet to form a web of elastic composite moving in the longitudinal or machine direction, the distributions generally extending in the machine direction (Step 1461). The method further entails periodically applying a core section on the moving elastic composite web (step 1462). Then, a top material sheet is continuously applied on the web including the core sections (step 1463). In the step of applying continuous distributions of elastics, at least two periodic distributions of elastics are established on the moving web by varying the lateral position of the distribution of elastics as the distributions are advanced in the machine direction toward the moving web of elastic composite (sub-step 1461A). In further embodiments, the step of applying the continuous distributions may include periodically varying the lateral position of the elastic distribution prior to engagement with the material sheet and further yet, periodically varying the lateral position to establish two sinusoidal patterns on the moving web of elastic composite.

Asymmetric Leg Cutouts

Figure 4A:
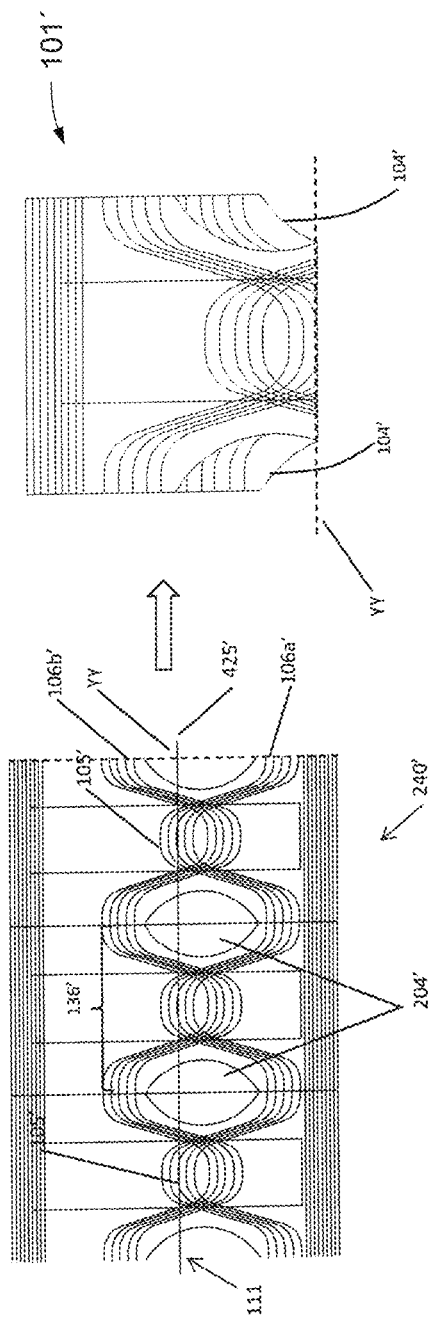
FIG. 4A is a simplified illustration of a web-based process for making an alternative disposable absorbent article. One or more aspects of the process shown and described with respect to FIG. 4A may be utilized to form the absorbent article shown and described with respect to FIGS. 19-24F.

FIG. 4A is a simplified representation of a web-based process of making a disposable absorbent article 101' according to the present disclosure (wherein like elements are referred to using like reference numerals). A variation of the process described in respect to FIGS. 2-4, this process may be employed to produce a modified disposable absorbent article 101'. This alternate process is particularly suited to making a modified pants product 101' having fitted leg openings 104'. FIG. 4A shows the moving web 240' of elasticized composite bodies 136' from which a disposable absorbent article 101' is derived. As described previously, the leg openings 104' are formed subsequent to the folding step by joining two linear segments 106*a'*, 106*b'* of the side edges of the elasticized composite body 136' and then sealing the union. The free non-linear cutout section (between the linear segments 106*a'*, 106*b'*) of the side edge substantially connect to form the leg openings 104'. In the finished absorbent pants product 101', each leg openings 104' may be described as having a front portion that is larger and extends further and arches higher than the back portion (e.g., as shown with the absorbent pants 101' in FIG. 4A). Thus, the front portion of the leg opening 104' rides higher on the thigh of the user than the back portion. In certain designs of the pants product 101', the asymmetric or uneven leg opening 104' enhances fit and comfort around the front thigh area of the user. This reduction in excess material on the front part of the pants, which is relatively flatter and less rounded than the back part when the pants are worn, allows for more room and discourages bunching and pinching on the front. The back portion of the leg hole fits lower and more snugly about the back of the wearer and, thus, preserves sealability and loading capacity in the back of the pants product.

As illustrated in FIG. 4A, the alternative pants product 101' is, in simplest terms, achieved by varying the leg hole cutout step. Specifically, holes 204' are punched out or otherwise cut into the web 240' at a position offset from the longitudinal centerline YY. With the circular cutouts in the previously described process, the cutouts are placed symmetrically about the longitudinal centerline YY and thus, about the fold line 425. For the exemplary pants product 101', a circular or elliptical cutout 204' is placed asymmetrically about the longitudinal centerline YY and lower relative to the longitudinal centerline. In FIG. 4A, the cutouts 204' provide an arc region below the longitudinal axis YY that is larger (in arc length and area) than the arc region provided above the longitudinal centerline YY. In the folding step, the web composite 240' is folded along the fold line 425, which corresponds to the longitudinal centerline YY, to form the leg opening 104'. As a result, the front part of the leg hole 104' is roomier and rides higher on the thigh of the wearer.

As with the previously described embodiments, periodic elastic distributions of elastic are directed about the leg cutouts 204' and leg openings 104'. The elastic distributions 111 form elastic annular regions about the leg holes 104', thereby enhancing fit and support. In this particular embodiment, the elastic distributions 111 that closely traverse the top of the leg cutouts exhibit a flatter pattern than the other elastic distribution.

In another variation, the leg cutout may be employed in a shape other than a circle. For example, an elliptical cutout may be employed to form a leg opening in the pants product that is sleeker or narrower than that resulting from a circular cutout. In either variation, a curvilinear elastic distribution may be applied to accommodate the leg cutouts and ultimately, provide an annular elastic region about each leg opening in finished pants product. The inventive method of elasticizing a moving web substrate is, therefore, shown to be well suited for providing annular elastic regions about leg openings of different shapes and locations on the web.

Shorts-Like Elasticized Pants Product

Figure 15A:
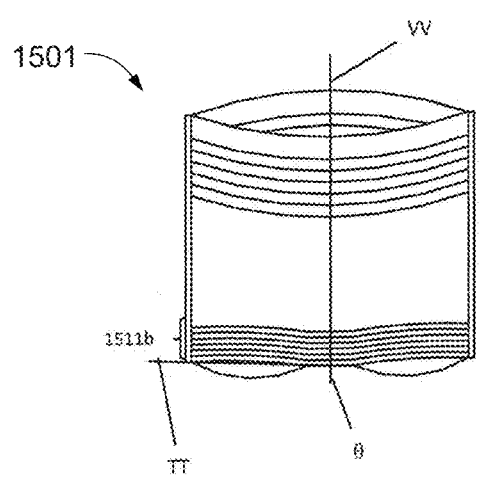
FIG. 15A is a simplified illustration in isometric view of a disposable absorbent article.
Figure 15B:
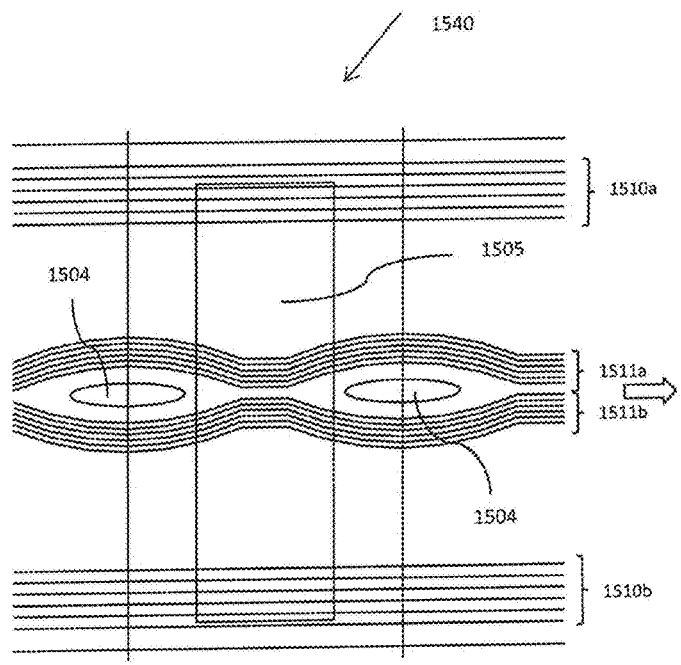
FIG. 15B is a simplified illustration of a web of elasticized composite bodies from which the article in FIG. 15A is derived.
Figure 16A:
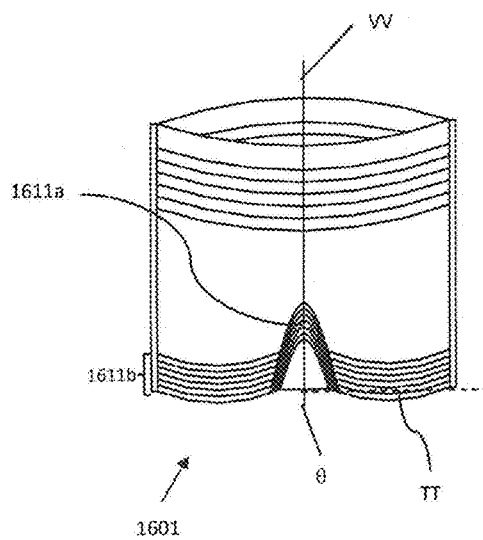
FIG. 16A is a simplified illustration in isometric view of a disposable absorbent article.

With reference to FIGS. 15A-15B and 16A-16B, a variation in the previously described method of making an absorbent pants product according to the disclosure will now be discussed. In this embodiment, the steps of applying distributions of elastics and providing leg cutouts in a moving web 1540 are modified to produce an alternative or modified pants product 1501. Two exemplary pants products 1501, 1601 are depicted in FIGS. 15A and 16A. The pants products feature a flatter or more horizontal leg opening 1504, 1604, which may be described by a leg opening angle Θ between the vertical centerline VV of the pants and a plane TT tangent to the leg opening. As compared to the previously described pants products, the leg opening angle Θ in these embodiments are rotated outward and closer to 90 degrees. In the pants product of FIG. 1, the angle Θ is close to about 45 degrees, whereas each of the pants product of FIGS. 15A and 16A features a leg opening angle that may be greater than about 75 to 80 degrees.

The simplified illustration of a moving web substrate in FIG. 15B shows the modifications to the elastic distributions 1511*a*, 1511*b* and the leg cutouts 1504 used in a process of making the pants product 1501. Firstly, the leg cutouts 1504 are not circular but are in the shape of relatively flat ellipticals. The short diameter of the elliptical is substantially less than the long diameter, creating a cutout 1504 that is more slit-like than a circular hole. Secondly, the elastic distributions 1511*a*, 1511*b* provided about the leg cutout 1504 is flatter and less sinusoidal. In this exemplary embodiment, the two elastic distributions 1511*a*, 1511*b* do not cross or overlap. The upper distribution of elastics 1511*a* stays above the longitudinal centerline YY and the lower elastic distributions 1511*b* is maintained below. The elastic distributions 1511*a*. 1511*b* are not completely flat, but feature a slight curvature while traversing the periphery of the leg cutout 1504. In any event, an annular elastic region about the leg opening 1504 is achieved. Pants product 1501 also includes core 1505 and elastic distributions 1510*a* and 1510*b*.

Figure 16B:
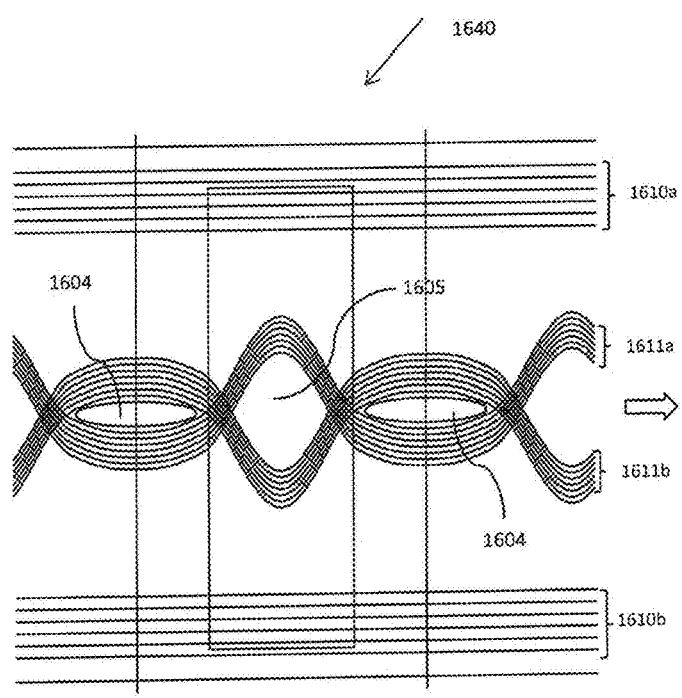
FIG. 16B is a simplified illustration of a web of elasticized composite bodies from which the article in FIG. 16A is derived.

Now referring to the simplified illustration of a moving web 1640 in FIG. 16B, the two sets of elastic distributions 1611*a*, 1611*b* intersect to create a more sinusoidal pattern around the area of the core 1605 or at least, a periodic pattern featuring alternating sections of high amplitude and low amplitude. In the area where the leg cutout 1604 is to be provided, however, the distribution of elastics is flatter and closely follows the elliptical slits 1604 in the web 1640. The intended crotch regions of the web 1640 are traversed by a pair of elastic distributions 1611*a*, 1611*b* of high amplitude. The elastics pass over and are concentrated on the upper extent and the lower extent of each elongated core placement. In this way, the elastics generally proximate the outside periphery of the core 1605. Article 1601 also includes elastic distributions 1610*a* and 1610*b*.

In either pants product, the resultant leg opening is described as being substantially circumferentially elasticized and featuring an elastic annular region. When worn, the annular elastic region substantially encircles the thigh of the user. In one respect, the pants product of FIGS. 15A and 16A are attributed with characteristics more akin to elasticated shorts (e.g., bike shorts). In this way, the pants product is provided with an encircling elasticized support about the thigh of the user. This circumferential support is generally more horizontal and focused lower than that of the leg hole of the pants product 101 in FIG. 1A. The circumferential engagement between each elasticized leg opening and the thigh of the wearer serves as an anchor point for the absorbent pants product. Together with the circumferential elastic annular region about the waist, the elastic annular regions around the leg opening actively seal the pants product about the body of the wearer. Importantly, support provided by the elasticized leg holes also provides enhanced support in the crotch region and core area of the pants product.

Gapping in the Elastic Distributions

In yet another aspect of the present disclosure, the system and method of making an elasticized absorbent product includes a modified step of applying multiple distributions of elastics on the moving web. As described previously, continuous distributions of elastics are applied generally in the machine direction. This includes applying and establishing at least two periodic or curvilinear distributions (generally in the machine direction) of elastics on the moving web by varying the lateral position of the elastics as the elastic distributions are advanced in the machine direction. Further to this step, continuous distributions of elastics may be applied to establish generally machine-directed distributions of elastic on each elastic composite body which have intermittent gaps (in the elastics). That is, a continuous, generally machine-directed distribution of elastic is applied, but the elastic strand on the finished composite web and on the final product is effectively segmented due to the intermittent gaps.

The locations of the gaps on the web are predetermined to correspond with desired gaps or absence of elastics in the final pants product. In some applications, the gap may be sufficiently wide to effectively de-elasticize the target area and in other applications, will be minimized to maintain continuity in the annular regions of elasticity in the final absorbent product. In one exemplary process, gaps in the elastic distributions are provided at locations on the web that correspond to the side edges of the pants product, whereupon the side seal or seams are formed. In yet another embodiment, gaps in the elastic distributions are located to coincide with the core location near the central or crotch region of the absorbent article. In this embodiment, it may be desired to disengage the core from the elastics and provide a relatively stable and unbiased core structure, or allow undisturbed placement of additional elements onto the core surfaces.

Figure 17:
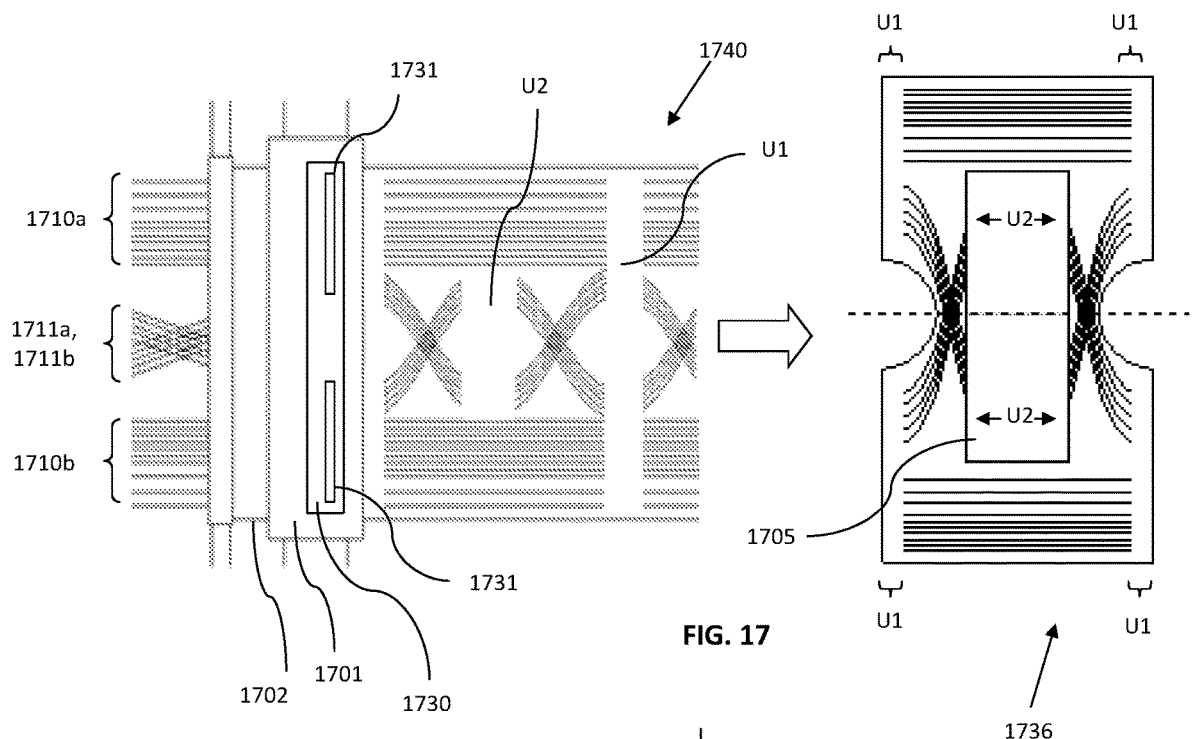
FIG. 17 is a simplified illustration of a system and process of applying elastic distributions on a web of elastic composite bodies. One or more of the system and method shown and described with respect to FIG. 17 may be utilized to form the absorbent article shown and described with respect to FIGS. 19-24F.
Figure 18:
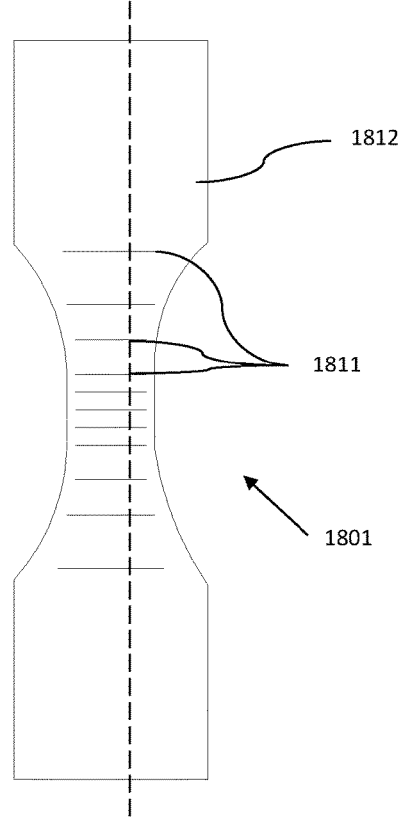
FIG. 18 is a simplified illustration of an elasticized core structure.

To exemplify these variations in the process and in the absorbent product of the disclosure, FIG. 17 provides a simplified illustration corresponding to the illustrations of FIGS. 2A-B and 4, with an elastic cutting or gapping step incorporated into the process. FIG. 17 shows the web 1740 of elastic composite delivered by rollers 1701 and 1702 and an elastic composite body 1736 severed from the web 1740. As shown in the moving elastic composite web 1740, multiple continuous distributions of elastics 1710*a*, 1710*b*, 1711*a*, 1711*b* are applied on the moving web with the two middle periodic elastic distributions 1711*a*, 1711*b* overlapping along the central portion of the web 1740. In this embodiment of the disclosure, the absorbent product is provided with gaps U1 along the proximity of the side edges or seams. The removal of elastics in this area provides a flat and consistent surface that may better accommodate a scaling operation, such as ultrasonic bonding or heat treatment. Furthermore, the flatter and more consistent surface, without shirring, may be deemed more aesthetically appealing in some product designs. In some applications, the gaps U1 will be minimized to ensure continuity of the annular elastic regions discussed previously.

As described previously, the distributions of elastics 1710*a*, 1710*b*, 1711*a*, 1711*b* may be applied on a nonwoven web of backsheet material as both input feeds engage a form roller 1701. Then, a web of intermediate nonwoven meets the form roller 1701 and is applied over the elastics to form a subsequent web featuring multiple continuous distributions of elastics sandwiched between two nonwoven webs. The elastics are subsequently cut or gapped by engagement of the form roller 1701 with a cutter roller 1730, and while retained in this sandwich and before the elasticized web meets the input feed of core section(s). Such lamination of the elastics helps to hold the elastics in place during and after cutting. In this technique, the elastics may be severed by pressing a blade of the cutter roller 1730 through the intermediate nonwoven layer and against the roller 1701, optionally with minimal puncture of the backsheet layer.

In one suitable arrangement, the form roller 1701 engages a second roller 1730 equipped with a set of blades or cutters 1731 for cutting the elastics, as known in the art. One suitable arrangement may be found in the specification of U.S. Pat. No. 4,525,229 (see e.g., FIG. 2). For the exemplary pants product design, a first pair of blades or cutters 1731 is spaced axially apart and has a lateral width sufficient to engage the extent of waist elastics. The cutters 1731 are, therefore, positioned near the ends of the cutter roller so as to correspond to the lateral locations of the waist elastic distributions on the web. In the depicted embodiment, the cutters 1731 are sufficiently axially long to reach and sever the middle elastic distributions 1711*a*, 1711 as well as waist elastics 1710*a*, 1710*b*. In further embodiments, two independent pairs of cutters may be employed, however, to minimize puncture of the nonwoven layers. A second pair of similarly spaced apart cutters (not shown) is provided just several degrees from the first pair of cutters 1731. The spacing between the two pairs is selected to correspond to the desired gap U1 on the moving web 1740 and to proximate the width (actually twice the width) of the desired side seam.

As known in the art, the speed of the cutter roller 1730 is synchronized with the rotation of the form roller 1701 so as to properly articulate the desired gapping. The cutters 1731 may further register with an anvil(s) provided on the form roller 1701 to make the desired cuts. In the depicted embodiment, the circumference of the form roller 1701 may correspond to four or five times the width of one pants product on the web 1740. Thus, the form roller 1701 is equipped with a number of properly spaced anvils, and the cutter roller 1730 will rotate at a rate that causes the cutters 1731 to engage the anvils.

In yet a further embodiment, the pants product may be freed of elastics in and around the location of the core 1705. A desired gap U2 has a width that approximates the width of the core 1705. Such a modification may be desired to provide stability and consistency to the core, including preventing any bunching of the core as well as the adjacent nonwoven sheet(s). In this particular design, only the two middle distributions of elastics 1711*a*, 1711*b* are gapped, as the waist elastics 1710*a*, 1710*b* do not encroach upon the intended area of the core 1705. The same roller 1730 as the one cutting the waist elastics, or another cutter roller, may be provided to engage the form roller 1701 and place intermittent gaps U2 in the two sets 1711*a*, 1711*b* of periodic or curvilinear elastic distributions. As the target distributions of elastics are typically closer to the center of the moving web, the cutters and matching anvils are also located near the center of the cutter roller 1730 and form roller 1701, respectively. To make the desired cut, two pairs of axially spaced apart cutters may be used or one longer cutter that extends from one elastic distribution to the other. Optionally, two successive pairs of cutters are provided that are spaced part in correspondence with the gap in the elastics.

Elasticized or Profiled Core Structures

In the systems depicted in each of FIGS. 2 and 6, as well as that described in respect to the process illustrated through FIGS. 3, 4 and 5, the core is delivered intermittently to the moving web pre-cut and oriented generally perpendicularly to the longitudinally moving direction of the moving web. As specifically shown in each of FIGS. 4 and 5, the pre-cut core is delivered on the web extending lengthwise between the longitudinal edges of the web, but in between each side edge (or severing line) of the elasticized composite. The core is, therefore, deposited in correspondence with its final location and orientation in the finished disposable absorbent product.

In many of the embodiments described herein, the inventive process is employed to apply a distribution of elastics across the width of each absorbent product, including over the core. The engagement or interaction between the elastics and the core may impart elasticity to the core, as required or desired by the design of the absorbent product. The resulting elasticized core may feature aesthetic and functional characteristics due to its elasticized regions. The benefits of elasticized core configurations have been discussed, for example, in U.S. Patent Application Publication No. US2011/0130736 A1, specifically FIGS. 6-9 in that publication (which application is assigned to an Assignee common with the Assignee of the present application and include, as inventors, one or more of the inventors named for the present application). One of the Figures is reproduced herein as FIG. 18 to illustrate an elasticated core structure 1801 (in a contracted state) achievable with the present inventive system and process. The core configuration includes a plurality of elastic distribution 1811 applied laterally in machine direction, and generally centrally on the moving web and across the core 1812. U.S. Patent Application Publication No. US2011/0130736 A1, and in particular FIGS. 6-9 thereof, and the descriptions accompanying those Figures, is incorporated herein by references for background purposes and made a part of the present disclosure. The common element in these referenced elasticized core designs is that elastics 1811 are directed and applied onto or proximate the core 1812 in the direction lateral to the lengthwise direction of the core 1812. In the present system and process, the application of elastics in the machine direction and centrally on the moving web, and the intermittent deposition of the core onto the web substrate in its ultimate position and orientation facilitate the provision of such an elasticized core. Moreover, the presently described system and process allow for variations in the elastic pattern applied to the core, including a plurality of different distributions or sets of elastics, spacing between the elastics, linear and/or curvilinear distribution patterns, including sinusoidal and other shapes.

The present system and process also allows for the cutting or gapping of the elastic distributions on the moving web and in the finished disposable absorbent product. In one embodiment, other curvilinear or periodic designs may be employed to distribute elastics about and proximate the periphery of the core and to encourage a pocket or cup shape in the core. The overlap of the two elastic distributions creates an annular elastic region along the periphery of the core, which can advantageously act as a type of O-ring seal. Such an elasticized O-ring may be designed in alignment with the user's bottom to improve absorption and retention. The elastic distribution shown in FIGS. 3-4 and 7-7A are two configurations suited for establishing such an annular elastic region and o-ring seal about the area of the core.

Several further variations in the process may be employed to engage the elastic distributions with the core. As discussed above, the elastic may not be applied directly to the core. For example, the elastic may be applied to the backsheet and situated between the backsheet and a second sheet or nonwoven. The resultant composite is then bonded with the core. With this composite, and specifically the backsheet directly engaging and connected with the core, the elastics within the backsheet composite act upon the core to create the desired elasticized and/or profiled shape. In another exemplary variation, the elastic may be applied to the backsheet and then the core is applied directly on top of the elastics (e.g., without an intermediate sheet). In any case, the elastic and sheet materials, and the core, are brought together on the form roller, and adhesive may be applied to the material sheets and elastics just before arrival at the forming roller.

In several of the core designs of FIGS. 6 and 7 in the referenced U.S. Patent Application Publication No. US2011/0130736 A1, the elastics are applied laterally and centrally on a rectangular core or in specific embodiments, in both or each of two overlapping cores. Elastication of the absorbent core structure, upon release of tension in the elastics, creates a narrowed central region of the elasticized core, which, as described in the referenced publication provides aesthetic and functional benefits in the absorbent product. In further embodiments, the spacing or pitch between successive elastics may be designed so as to create more of a concave narrowed central region. This may be achieved, for example, by placing a higher concentration of elastics along the center and a lower concentration away from the center (see e.g., FIGS. 7C-D in the referenced publication). The elastics may be strategically placed between a stack of cores and other materials to provide the profiled core configurations in FIG. 8 (of the referenced publication) as well as the corrugated configuration of FIG. 9 (in the referenced publication).

Elastic Composite Web Forming Mill

Figure 10:
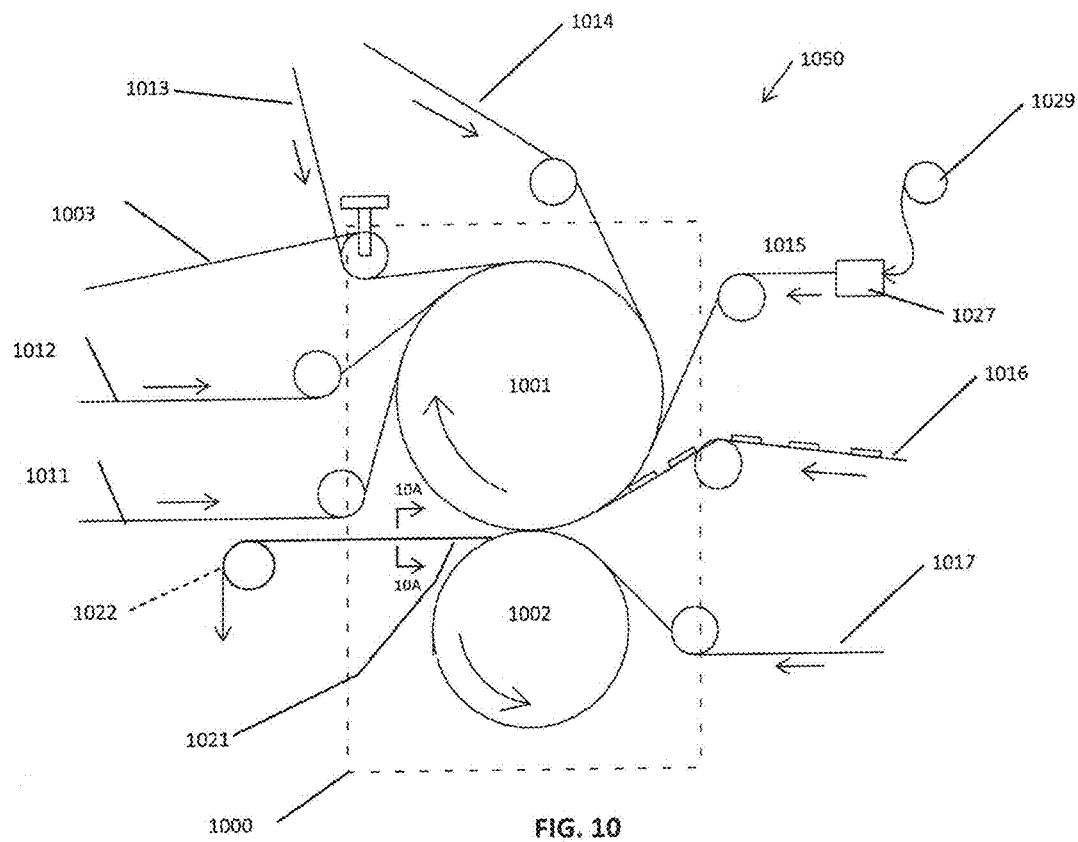
FIG. 10 is a simplified schematic representation of a system for making a disposable absorbent article. One or more portions of the system shown and described with respect to FIG. 10 may be utilized to form the absorbent article shown and described with respect to FIGS. 19-24F.

FIG. 10 is provided as a simplified physical representation of a system 1050 according to the disclosure, and more specifically, an elastic composite web forming or joining mill 1000 of the system. The area (or region) inside the dashed box represents, in one aspect of the inventive system 1050, a centralized conglomeration of web components and system machine components, from which the desired web 1021 of discrete elastic composite bodies are outputted. The inventive system 1050 may be described as comprising a plurality of feed lines that converge on the joining mill 1000 in a predetermined manner to produce the predetermined moving web substrate 1021. The input feed lines are managed to direct a component of the product at a rate, speed, orientation, and lateral placement required of the web substrate product. Some input feed lines may be associated with "cut and place" units that intermittently apply a discrete unit of material to the moving web. Furthermore, the input feed lines are managed to converge and engage other input feed lines in the desired sequence and rate.

With the system 1050 in FIG. 10, each of the elements of the web substrate is optionally applied to the mill 1000 linearly or inline in the machine direction. Accordingly, all feed lines and output lines can approach the mill 1000 from the right or left, or the top of the mill 1000, but within a lateral window not exceeding the axial length of the form roller 1001 (and, in some micro-applications, not substantially wider than the width of the web substrate 1021). This physical characteristic of the system 1050 promotes manageability and flexibility in the process, including the ability to modify the properties of the finished absorbent product. The inventive system, and more particularly the mill 1000, also displays a small footprint. The mill 1000 also lends itself to being packaged as a modular, self-contained unit.

Figure 10A:
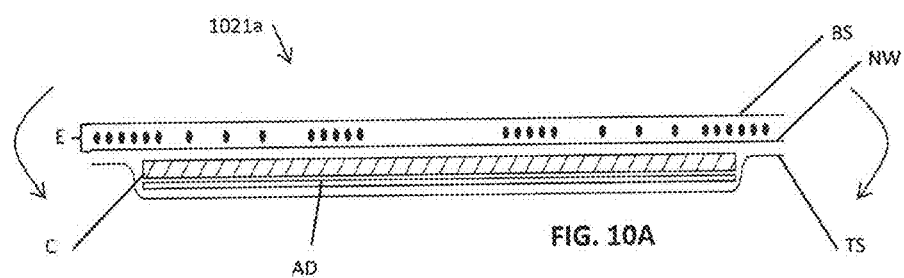
FIG. 10A is a cross-sectional view of a web of elastic composite bodies.

In one embodiment of the disclosure, a web substrate product 1021a is outputted by the mill 1000 as shown in the lateral cross section of FIG. 10A. Upon output from the mill 1000, the moving web substrate 1021a comprises a layer of topsheet TS on the bottom, an AD (acquisition and distribution) layer above the topsheet TS, and a series of individual, elongated cores C above the AD layer. Above this, a sandwich is provided of an intermediate nonwoven layer NW, a layer of backsheet BS, and various elastic distributions E therebetween. Directional arrows in FIG. 10 indicate the direction toward which the composite web 1021a is folded. As shown, the web 1021a is folded such that the topsheet layer TS rotates toward itself and is ultimately positioned on the inside of the folded web. In the finished absorbent article as worn, the topsheet TS is placed adjacent the body of the wearer.

After emerging from the mill 1000, the web substrate 1021a may be folded, sealed, and cut to produce the disposable absorbent article. These subsequent steps are considered post-joining steps that are implemented after delivery or output of the web 1021a. The folding step is performed at a folding station 1022 comprising of angular directional bars that are located immediately forward of rollers 1001, 1002. The folding station 1022 directs the web 1021 to a series of turns that flips and folds the substrate 1021a. Once folded, the leg holes are cut out, the side seams are sealed together, and then, the web substrate is severed along the seams (to produce discrete pants products). These steps have been discussed in respect to FIGS. 4 and 5, for example. Additional, pre-packaging steps may also be employed after the sealing and severing steps. In alternative embodiments, the step of cutting or punching the leg cutouts may be provided before the folding station 1022 and immediately after delivery of the web substrate output 1021a.

It should be noted that the post-joining steps may be modified so as to provide for a diaper product, as opposed to a pants product. In such a variation, the side seam sealing step may be eliminated. In this respect, the web substrate output may only require the severing step to product discrete diaper products. In a further variation of the system, process, and product that is derived from the inventive system and process, the web substrate outputted by the joining mill may be folded in the reverse direction to produce a modified pants product or diaper. Such a product objective may require modifications to the input feed lines to the joining mill, as further described below.

Referring now to FIG. 10 and well as FIG. 10A, several stages of the joining process are described as a sequence of joining various components of the web substrate 1021a. The primary components of the mill are a main or forming roller 1001 and a corresponding secondary roller 1002. As shown in FIG. 10, an input feed 1011 of backsheet material is engaged by the forming roller 1001 as well as the distributions 1012 of waist elastics and distributions 1013, 1003 of curvilinear elastics (as previously described in more detail in respect to FIGS. 2A and 2B). The moving web of elastics applied to the backsheet is then engaged from above by an input feed 1014 of intermediate nonwoven. This engagement sandwiches the elastics within the backsheet and intermediate nonwoven. In further embodiments, a cutter roller may be added to engage the form roller and to selectively cut one or more of the elastic distributions sandwiched by the backsheet and intermediate nonwoven.

The resultant elasticized web then engages the input feed 1016 of spaced apart and laterally oriented cores. As described previously, the cores are spaced in correspondence with a central position on the final pants product and in alignment with the longitudinal centerline of the moving webs and the forming roller 1001. The cores are optionally delivered pre-cut in an elongated rectangular form that is lengthwise to the longitudinal or machine direction. A cutting roller machine 1027 is provided upstream of the rollers 1001, 1002 and receives a continuous feed of sheet core material 1015 from a supply roll 1029. Optionally, a second input feed 1016 of a second core or an ADL layer is directed atop and upon the resultant elasticized composite (with core). In this instance, an input feed 1017 of the topsheet engages the elastic composite (with cores) to provide a topsheet layer over the core material(s). The resultant product is a moving web substrate 1021 of an elasticized absorbent composite that may be further processed to produce a pants product or a diaper product.

In this system configuration, the web substrate 1021a is delivered with the backsheet BS on top and the topsheet TS on the bottom. The continuous web 1021a is the optionally passed to the folding station 1022, which effectively flips and folds the web 1021a. From there, the side seams of the web 1021a may be sealed and then severed, to produce discrete elastic composite bodies.

Reversed Elastic Composite

Figure 10B:
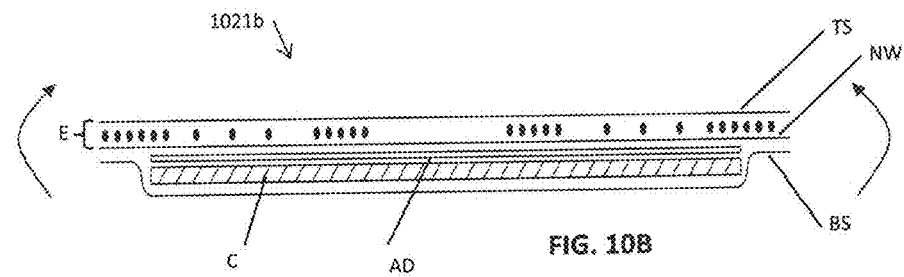
FIG. 10B is a cross-sectional view of an alternative web of elastic composite bodies.

In a further embodiment, an alternative disposable absorbent product is produced by the system and process by modifying the input feed lines to the joining mill 1000. Such an alternative moving web substrate 1021*b* of elasticized composite bodies is depicted in FIG. 10B in lateral cross-section. The moving web 1021*b* outputted by the joining mill 1021 provides a topsheet layer TS as a top layer and multiple distributions of elastics E sandwiched between the topsheet layer TS and an intermediate nonwoven layer NW. The core C, the ADL layer AD, and the backsheet layer BS fill out the rest of the elastic composite. Referring to FIG. 10, such a composite web 1021*b* may be achieved by switching, for example, the topsheet feed 1017 with a backsheet source and perhaps, as necessary switching the ADL and core input feed sources. Finally, the resultant web substrate is folded in the reverse direction (see fold directional arrows) such that the elastic distributions E are inside of the core C. By placing the elastics closer to the user, the topsheet TS is drawn closer to and about the body of the wearer and the elasticized composite 1021*b* will tend to support and accommodate the contour of the wearer's body. The improved engagement of the topsheet TS about the wearer not only enhances fit, but the topsheet TS is better positioned to prevent leakage. In further embodiments, the inventive process may be employed to apply sinusoidal or other curvilinear elastic distributions about the periphery of the core, thereby creating an elasticized pocket about the topsheet/intermediate nonwoven sub-composite or the core. The incorporation of such an upwardly biased pocket may also be conducive to the use of one or more central apertures for disposal into the space between the core and the topsheet/intermediate nonwoven.

Article with Elastic Distribution Surrounding an Opening at the Absorbent Core

FIGS. 19-24F depict embodiments of an absorbent article having an elastic distribution that surrounds an opening at the absorbent core, and a system and methods for making the same. The embodiments depicted and described with respect to FIGS. 19-24F may be combined with one or more elements of any of the various other embodiments described in the present disclosure, including those described with reference to FIGS. 1-18. For example the elastic distributions and methods and systems of applying them as shown in FIGS. 1-18 may be combined with the one or more of the elements described with reference to FIGS. 19-23.

FIGS. 19-23 depicts embodiments that include multiple features, including an annular cuff, one or more openings, an unbonded zone and bonded zone, an inner elasticated chassis, and an outer elasticated chassis; however, one skilled in the art would understand that the embodiments disclosed herein are not limited to include each and every feature as shown in FIGS. 19-23, and that one or more of these features may be included or left out in certain embodiments. FIGS. 19-23 depict various embodiments of an absorbent article include an inner elasticated chassis, an outer elasticated chassis, an absorbent member, and an annular cuff (cuff 2001) formed about the absorbent member. While not limited to including additional features, in some aspects, the absorbent article further includes one or more openings (opening 2165) formed through the inner elasticated chassis. In some aspects, the absorbent article further includes one or more bonded zones 2161 and one or more unbonded zones 2163, optionally in combination with the one or more openings 2165. In some aspects, the outer elasticated chassis of the absorbent article is elastically coupled with the inner elasticated chassis, optionally in combination with the one or more bonded zones 2161 and one or more unbonded zones 2163, and optionally in combination with the one or more openings 2165.

Figure 19:
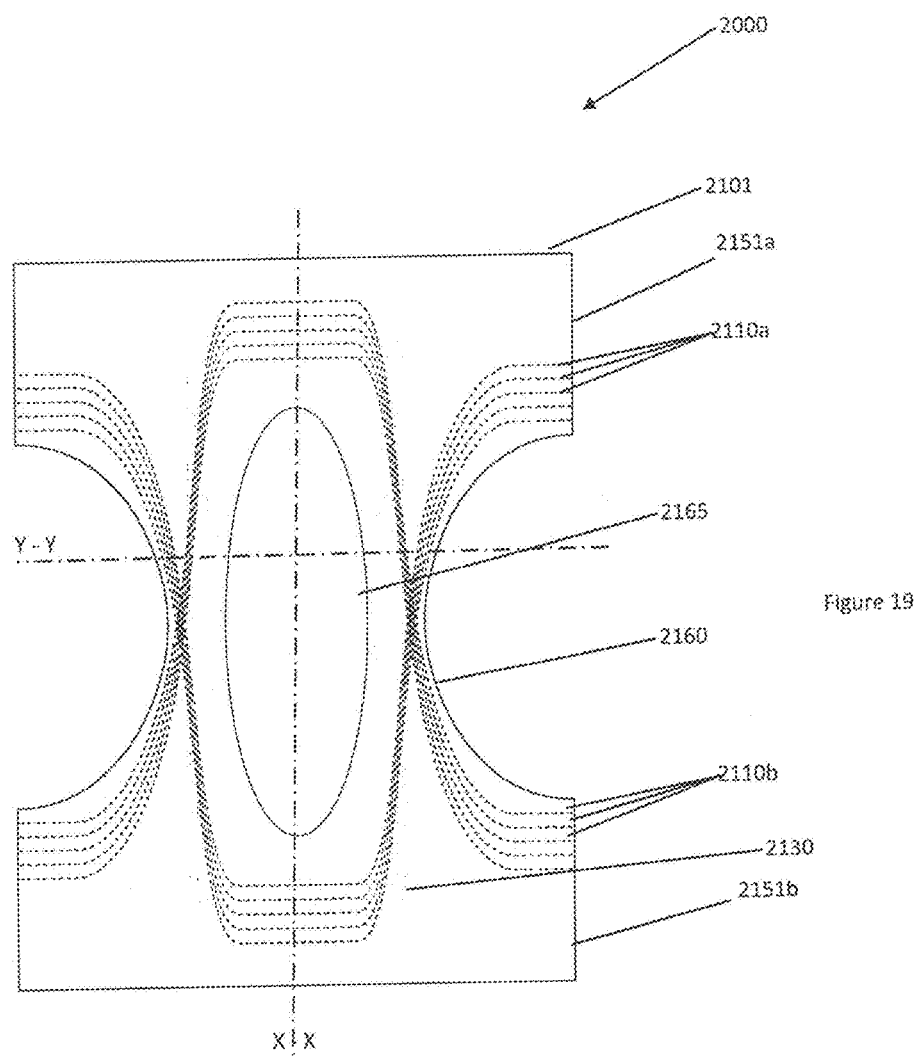
FIG. 19 is a plan view of an absorbent article having an elastic distribution surrounding the absorbent core in accordance with certain embodiments of the present disclosure.
Figure 20B:
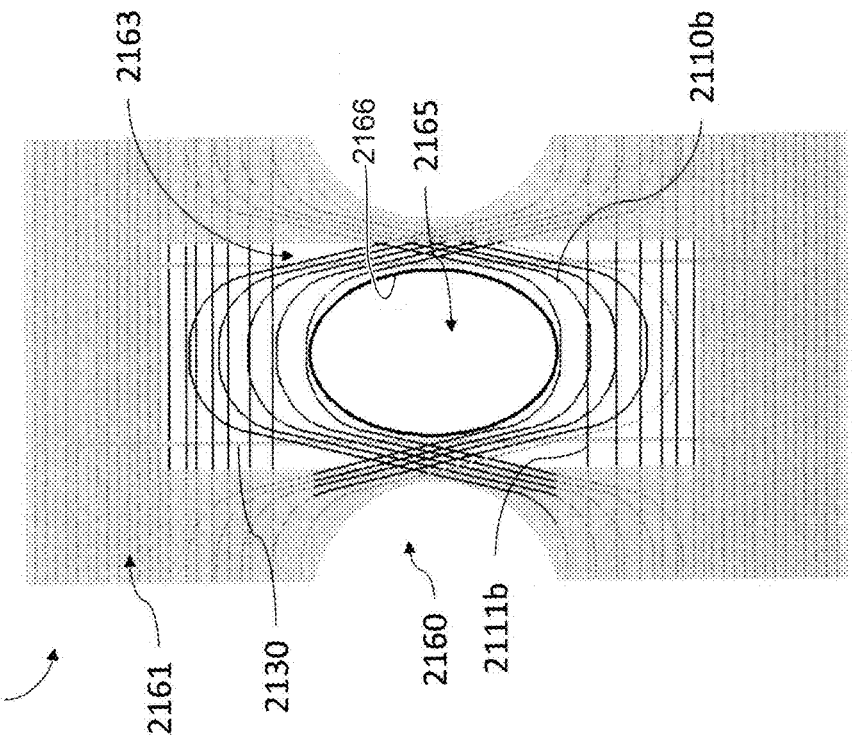
FIG. 20B is a plan view showing the arrangement of bonded and unbonded zones in the absorbent article of FIG. 19.
Figure 20A:
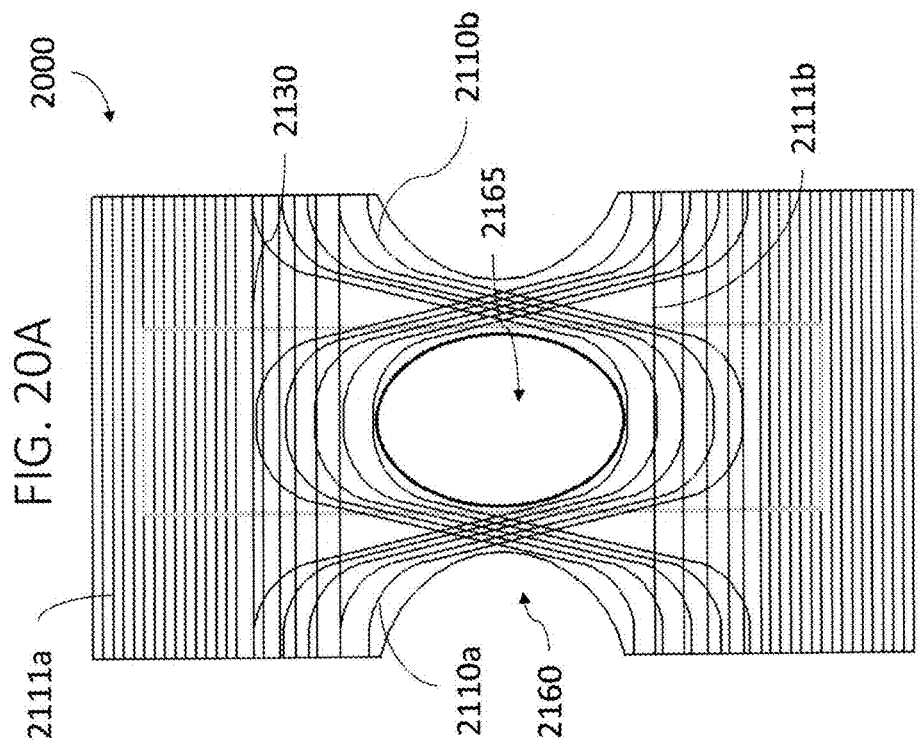
FIG. 20A is a plan view showing the arrangement of elastics in the absorbent article of FIG. 19.

FIG. 19 is a plan view of an absorbent article having an elastic distribution surrounding the absorbent core in accordance with certain embodiments of the present disclosure, FIG. 20 is an exploded view showing the different layers of the absorbent article of FIG. 19, FIG. 20A is a plan view of an absorbent article showing the relative placement of the elastics in the inner and outer elasticated constructions, and FIG. 20B is a plan view of an absorbent article showing the bonded and unbonded zones between the inner and outer elasticated constructions.

With reference to FIGS. 19, 20, 20A and 20B, absorbent article 2000 may include an inner elasticized construction, including inner sheet 2101. Inner sheet 2101 may be a nonwoven sheet. When worn by a user, inner sheet 2101 may be positioned on the body-side of absorbent article 2000, facing the skin of the user. The inner elasticized construction of absorbent article 2000 also includes inner support sheet 2102. Inner support sheet 2102 may be a nonwoven sheet. One or more sets of elastic strands 2110*a* and 2110*b* are distributed between inner sheet 2101 and inner support sheet 2102. In some embodiments, the sets of elastic strands 2110*a* and 2110*b* overlap one another. In certain embodiments, the sets of elastic strands 2110*a* and 2110*b* are arranged in an overlapping, sinusoidal or wave-like pattern. As shown, absorbent article 2000 includes two elastic strands, 2110*a* and 2110*b* that overlap in a sinusoidal or wave-like pattern. In some embodiments, the sets of elastic strands 2110*a* and 2110*b* do not overlap one another. Each set of elastic strands 2110*a* and 2110*b* may include one or more elastic strands. In some embodiments, spacing between each strand of the sets of elastic strands 2110*a* and 2110*b* varies. In other embodiments, spacing between each strand of the sets of elastic strands 2110*a* and 2110*b* does not vary. For example, and without limitation, the spacing between elastic strands of the sets of elastic strands 2110*a* and 2110*b* may be greater at or near the waist edges of absorbent article 2000, and less at or near crotch region 2113 of absorbent article 2000. Elastic strands 2110*a* and 2110*b* may be incorporated into or onto inner elasticated construction, such as via hot melt adhesive, ultrasonic bonding, thermobonding technologies, or any combination of these bonding methods. While shown and described as being sandwiched between two sheets (inner sheet 2101 and inner support sheet 2102) elastic strands 2110*a* and 2110*b* may be incorporated into inner elasticized construction in other configurations. In some aspects, elastic strands 2110*a* and 2110*b* may be: bonded or otherwise incorporated into inner sheet 2101 and not inner support sheet 2102; bonded or otherwise incorporated into inner support sheet 2102 and not inner sheet 2101; or bonded or otherwise incorporated into both inner sheet 2101 and inner support sheet 2102. Sheets 2101, 2102, 2103, and 2104 are also referred to herein as fabric layers.

Absorbent article 2000 may include one or more openings 2165*a* and 2165*b* (e.g., holes, through-holes, apertures) formed through one or more portions of inner sheet 2101 and/or one or more portions of inner support sheet 2102. In certain embodiments, openings 2165*a* and 2165*b* are located in the space between the sets of elastic strands 2110*a* and 2110*b* (i.e., within the space defined by the overlap regions between the sets of elastic strands). In some such embodiments, sets of elastic strands 2110*a* and 2110*b* do not intersect openings 2165*a* and 2165*b*. In other embodiments, sets of elastic strands 2110*a* and 2110*b* at least partially intersect openings 2165*a* and 2165*b*. In certain embodiments, openings 2165*a* and 2165*b* are in the shape of an oval, circle, square, rectangle, or any other shape or approximation thereof. In some embodiments, the shape of pattern of the sets of elastic strands 2110a and 2110b matches the dimensions of openings 2165a and 2165b and dimensions of leg cuffs 2160 cutouts, such that the sets of elastic strands 2110a and 2110b surround the edge of openings 2165a and 2165b. In some embodiments, the pattern of the sets of elastic strands 2110a and 2110b surrounding the edge of openings 2165a and 2165b match or approximately match the periphery of absorbent member 2130. Thus, the openings 2165a and 2165b may be coincident, or at least partially coincident, with the space defined by the overlap regions (e.g., Ox) between the sets of elastic strands 2110a and 2110b. In some aspects, the pattern of the sets of elastic strands 2110a and 2110b form an annular elastic region adjacent a periphery of the absorbent member 2130 and a periphery of the openings 2165a and 2165b. The elastic strands 2110a and 2110b at the annular elastic region may be elastically coupled with (e.g., bonded with, adhered to, or otherwise attached to) the absorbent member 2130, the underlying layers of the chassis (e.g., the inner support sheet or portions of the outer elasticated chassis), or combinations thereof. The elastic strands 2110a and 2110b may thus impart elastic forces to the absorbent member 2130 and/or the underlying layers of the chassis, thereby biasing the periphery of the absorbent member 2130 upwardly, biasing the underlying layers of the chassis upwardly, or combinations thereof. Such biasing of the absorbent member 2130 and/or the underlying layers of the chassis may form a cuff positioned about the periphery of the absorbent member 2130 and openings 2165a and 2165b, as discussed in more detail below.

In some embodiments, a length (or diameter) of opening 2165a and 2165b (i.e., longitudinal dimension along or parallel to line X-X) is from 10% to 95%, or from 20% to 85%, or from 30% to 65%, or from 40% to 55% as long as the total length of absorbent article 2000 or greater than 50% of, or more preferably, 60% or 66% of the length of article 2000. In some embodiments, a width (or a diameter or minimum diameter, in case of some elliptical shapes) of opening 2165a and 2165b (i.e., lateral dimension along or parallel to line Y-Y) is from 10% to 90%, or from 30% to 80%, or from 40% to 70%, or from 30% to 60%, or from 40% to 50% as wide as the narrowest part of absorbent article 2000. In some aspects, the area defined by opening 2165 ranges from about 30% to 90%, or from 40% to 80%, or from 50% to 70% of the area (surface area) defined by the top surface ("A" as shown in FIG. 20) of absorbent member 2130 and more preferably, 60% or 66% as wide as the narrowest part of absorbent article 2000. As shown in FIG. 20, absorbent member 2130 is generally rectangular, such that the area is defined by multiplying the length of one of the side edges (lateral edges "E" and "D") with the length of one of the front or rear edges (edges "B" and "C", end regions). Edges "B", "C", "C", and "E" define the periphery of the absorbent member 2031. As shown in FIG. 20, the opening 2165 is generally oval, such that the area can be determined by multiplying x by r1 and r2, where r1 is the "short radius" of the oval and r2 is the "long radius" of the oval. One skilled the art would understand that the absorbent member 2130 and opening 2165 are not limited to these particular shapes. The narrowest part of absorbent article 2000 may be crotch region 2113. For example and without limitation, for embodiments in which absorbent article 2000 is a baby diaper, opening may have a length ranging from 150 mm to 400 mm and a width ranging from 60 mm to 110 mm at its widest point. One skilled in the art would understand that the absorbent article disclosed herein is not limited to these particular dimensions, and may any of a variety of dimensions depending upon the particular application. In some aspects, the openings 2165a and 2165b expose the bodyside of the absorbent member 2130.

Absorbent article 2000 includes an outer elasticized construction. The outer elasticized construction includes outer sheet 2104 and outer support sheet 2103, each of which may be a nonwoven sheet. In some aspects, the outer elasticized construction does not have an opening, hole, through-hole, or aperture as does the inner elasticized construction. While both the inner and outer elasticized constructions are depicted and described herein as being multi-layer constructions (e.g., inner/outer sheet and inner/outer support sheet), one or both of the inner and outer elasticized constructions may be a single layer construction. Furthermore, while both the inner and outer constructions are depicted and described herein as being elasticized constructions, one of the inner or outer elasticized constructions may be a non-elasticized construction.

One or more outer elastic strands 2111 may be located between outer sheet 2104 and outer support sheet 2103. In some embodiments, elastic strands 2111 may be arranged in a parallel or generally parallel manner. In certain embodiments, elastic strands 2111 may extend laterally (i.e., along Y-Y) within absorbent article 2000, parallel to the front and rear waist edges of absorbent article 2000. One or more portions of absorbent article 2000, such as crotch region 2113, may be free of elastic strands 2111. In some embodiments, spacing between elastic strands 2111 varies. In other embodiments, spacing between elastic strands 2111 does not vary. For example, and without limitation, the spacing between elastic strands 2111 may be greater at or near the waist edges of absorbent article 2000.

In certain embodiments, the inner and outer elasticised constructions form a chassis of the absorbent article.

Between the inner and outer elasticised constructions, absorbent article 2000 includes absorbent member 2130. Absorbent member 2130 may be an assembly of a topsheet layer, backsheet layer, and absorbent core. The absorbent core may be located between the topsheet layer and the backsheet layer. In some embodiments, the topsheet layer may be a hydrophilic, water permeable nonwoven, and the backsheet layer may be a water impermeable film, as described elsewhere herein. The absorbent core may be or contain one or more absorbent materials, including but not limited to fluff pulp, nonwoven, superabsorbent polymer particles, acquisition distribution nonwoven layers, distribution nonwoven layers, and tissue. In some embodiments, leg cuffs 2160 may be formed via cutouts in both the inner and outer elasticized constructions.

Each layer of absorbent article 2000, including inner sheet 2101, inner support sheet 2102, outer sheet 2104, outer support sheet 2103, and absorbent member 2130, may be bonded and/or adhered to adjacent layers using hot melt adhesive, ultrasonic bonding, thermo-bonding technologies, or any combination of these bonding methods. With reference to FIG. 20B, in certain embodiments, the inner elasticized construction (e.g., inner support sheet 2102) is only partially bonded to absorbent member 2130 (e.g., the topsheet layer thereof) and/or to the outer elasticized construction, such that unbonded elasticized portions of the inner elasticized construction are configured to rise up freely away from absorbent member 2130 and/or the outer elasticized construction when absorbent article 2000 is worn. As shown in FIG. 20B, inner elasticized construction is bonded, optionally continuously bonded, to the outer elasticated construction within bonded zone 2161 (as shown in gray), and is unbonded (not bonded) to the outer elasticated construction within unbonded zone 2163. In some aspects, the bonded zone 2161 at least partially overlaps with absorbent member 2130, such that the inner elasticated construction is bonded with the absorbent member 2130 within the bonded zone 2161. In other aspects, the bonded zone 2161 does not overlap with absorbent member 2130, such that the inner elasticated construction is not bonded at all to the absorbent member 2130. Areas of inner elasticized construction that are not bonded (unbonded zone 2163) to absorbent member 2130 or the outer elasticized construction may be free to move vertically relative to absorbent member 2130 (e.g., vertically along direction 5000). For example, and without limitation, a region of the inner elasticized construction (e.g., inner support sheet 2102) around opening 2165 may be substantially unbonded to the underlying layers of the product (e.g., outer sheet 2104 and absorbent member 2130). In some such embodiments, absorbent article 2000 may be generally configured in a U-shape around the body of the user. The unbonded surface area of the inner elasticized construction a portion of surface area of the bottom surface of the inner elasticized construction that is free of bonding to the any underlying structure, such as the absorbent member 2130 and the outer elasticized construction. Thus, this unbonded surface area may move without impedance from the underlying structure.

Figure 20C:
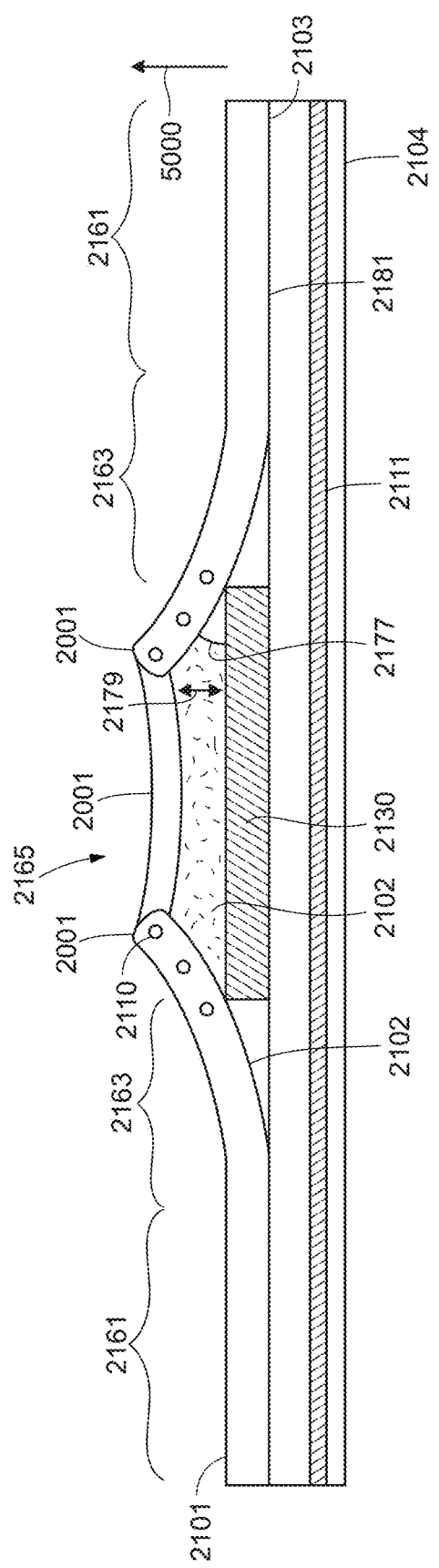
FIG. 20C is a cross-sectional view showing the cuff formed around the absorbent member of FIG. 19.

With reference to FIGS. 20A, 20B and 20C, the formation of a cuff (also referred to herein as a barrier or dam) about absorbent member 2130 will be discussed. As will be detailed below each of the followed elements dynamically and synergistically contributed to the formation of cuff 2001, including: (1) elastics 2110 of the inner elasticated construction; (2) elastics 2111 of the outer elasticated construction; (3) opening 2165; (4) bonded zone 2161; and (5) unbonded zone 2163.

Contraction of elastics 2110a and 2110b of the inner elasticated construction imparts a force onto the sheet layers of the inner elasticated construction (i.e., sheets 2101 and 2102) that is directed generally towards the center of opening 2165 and along axis Y-Y as shown in FIG. 19. As a portion of the inner elasticated construction is not bonded to the underlying absorbent member 2130 and the outer elasticated construction, this portion of the inner elasticated construction is free to move relative to the underlying absorbent member 2130 and the outer elasticated construction, while movement of the bonded portions of the inner elasticated construction is restrained due to the bonding. Thus, the contraction of elastics 2110a and 2110b results a drawing force upon at least the unbonded portions of the inner elasticated construction generally towards the center of opening 2165 and along axis Y-Y. The contraction of elastics 2110a and 2110b may thus position the layers of the inner elasticated construction over the absorbent member, or further over the absorbent member than prior to contraction, such that opening 2165 is positioned entirely within the perimeter of absorbent member 2130.

Additionally, the unbonded portions of the inner elasticated construction are free to move vertically relative to the absorbent member 2130 along direction 5000, as this portion is not restrained via bonding with the underlying absorbent member 2130 and the outer elasticated construction. This unbonded portion of the inner elasticated construction forms a flap of fabric that is free to move and/or curl upwards along direction 5000 relative to the underlying absorbent member 2130 and the outer elasticated construction. In some aspects, the length of flap, that is the length of the unbonded portion of the inner elasticized construction from the edge of opening 2165 to the edge of the bonded region 2161 controls the maximum height of cuff 2001. As shown in FIG. 20C, cuff 2001 is lifted to height 2179 and is at an angle 2177 relative to the top surface of absorbent member 2130. Also shown in FIG. 20C is adhesive 2181 bonding the inner and outer elasticized constructions together at bonding zones 2161.

Opening 2165 provides access to absorbent member 2130 for insult, as inner elasticated construction may be formed of hydrophobic materials. Additionally, openings 2165 allows or at least assists the inner elasticated construction to rise upwards relative to the underlying absorbent member 2130 and the outer elasticated construction to form cuff 2001.

The elastics 2111 of the outer elasticated construction are elastically coupled to (i.e., capable of transferring elastic forces to) the inner elasticated construction via the bonded zones 2161. Elastics 2111 also contract generally towards the center of opening 2165 and along axis Y-Y. As elastics 2111 contract, this imparts force onto the outer elasticated chassis, drawing the outer elasticated chassis generally along axis Y-Y and towards axis X-X. Also, at least some elastic force resulting from the contraction of elastics 2111 is imparted to the inner elasticated chassis at the bonding zone 2161. As unbonded zone 2163 of the inner elasticated chassis is not elastically coupled to elastics 2111, movement of the bonded portions of the inner elasticated chassis caused via contraction of elastics 2111 results in the "bunching up", gathering, and/or shirring of the unbonded portions of the inner elasticated chassis (i.e., the flap); thereby, assisting in the formation of the cuff 2001. Furthermore, at least some of elastics 2111 are positioned directly below absorbent member 2130 (e.g., elastics 2111b). Such elastics of outer elasticated chassis that are positioned directly below absorbent member 2130, when contracted, impart elastic forces to absorbent member 2130, causing the width of absorbent member 2130 to be reduced. Elastics 2111 may vary in pitch along different portions of the outer elasticated chassis. As shown in FIGS. 20A and 20B, elastics 2111 are more closely spaced near the back and waist end edges, and are less closely spaced near the crotch region and under absorbent member 2130. Elastics 2111 are not limited to this configuration, and may have a differently varied pitch or an even pitch. In some aspects, instead of or in addition to varying the pitch of elastics 2111, the denier of elastics 2111 is varied. Elastics 2111 also urge the absorbent article into a U-Shape configuration via contraction, which may cause further gathering of the unbonded portions of the inner elasticated construction, assisting in the creation of and/or enhancement of cuff 2001.

As such, the drawing-in of the inner and outer elasticated constructions via contraction of elastics 2110 and 2111 results in a shrinking of opening 2165 (e.g., if opening were a circle, the diameter of the opening would be reduced) and a rising of the "flap" of the unbonded portion of the inner elasticated construction to form cuff 2001.

In some aspects, the upwardly biased portions of the inner elasticated construction created, in part, by the annular elastic region of elastic strands 2110a, 2110b form cuff 2001, optionally as a complete or substantially complete cuff or barrier positioned about absorbent member 2130 when absorbent article 2000 is worn. In such embodiments, the upwardly biased portions of the inner elasticated construction complete or substantially surround and/or enclose (e.g., 360 degree cuff) the absorbent member 2130. In use, cuff 2001 may prevent leakage of urine and/or feces out of absorbent article 2000, as well as instill user confidence in product performance. Embodiments of cuff 2001 (e.g., that provide 360° enclosure of absorbent member 2130) are capable of stopping leakage out of the sides, front and back of absorbent article 2000. In contrast, longitudinal, straight leg cuffs may only prevent leakage along the sides. As such, formation of cuff 2001 may avoid the need to add any separate dam or cuff structure at the front and rear of absorbent article 2000. Such cuffs 2001 may be an integral portion of the inner elasticized construction, and not a separate, discrete element mechanically fastened thereon. As such, absorbent article 2000 may have a self-cuffing core, with self-sealing, integrated cuffs 2001. In operation, the chassis and elastics strands of absorbent article 2000 may directly and selectively elasticize, urge, conform, and/or shape selected portions of absorbent member 2130.

Figure 21:
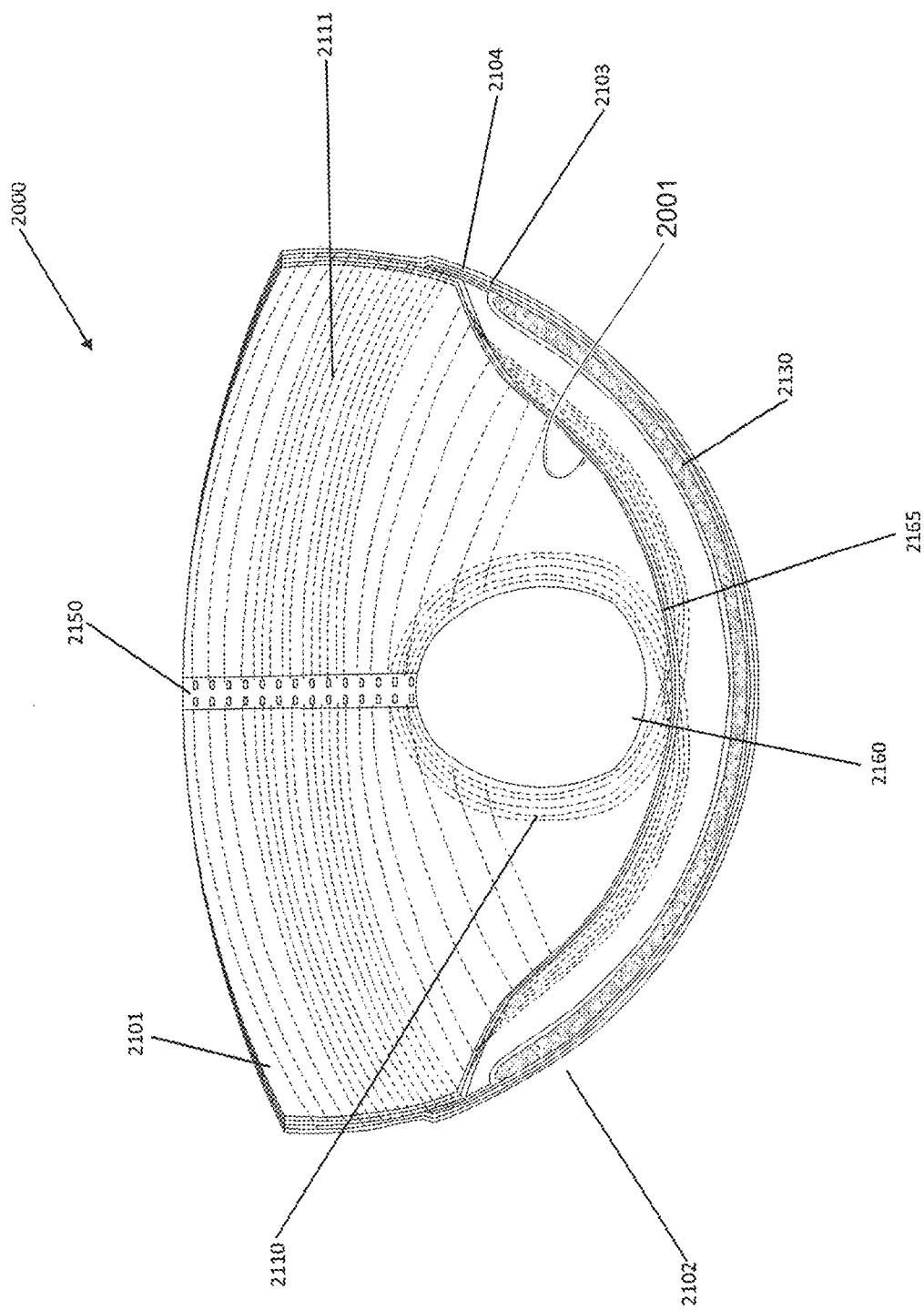
FIG. 21 is a cross-sectional view, along line X-X, of the absorbent article of FIG. 19.
Figure 22:
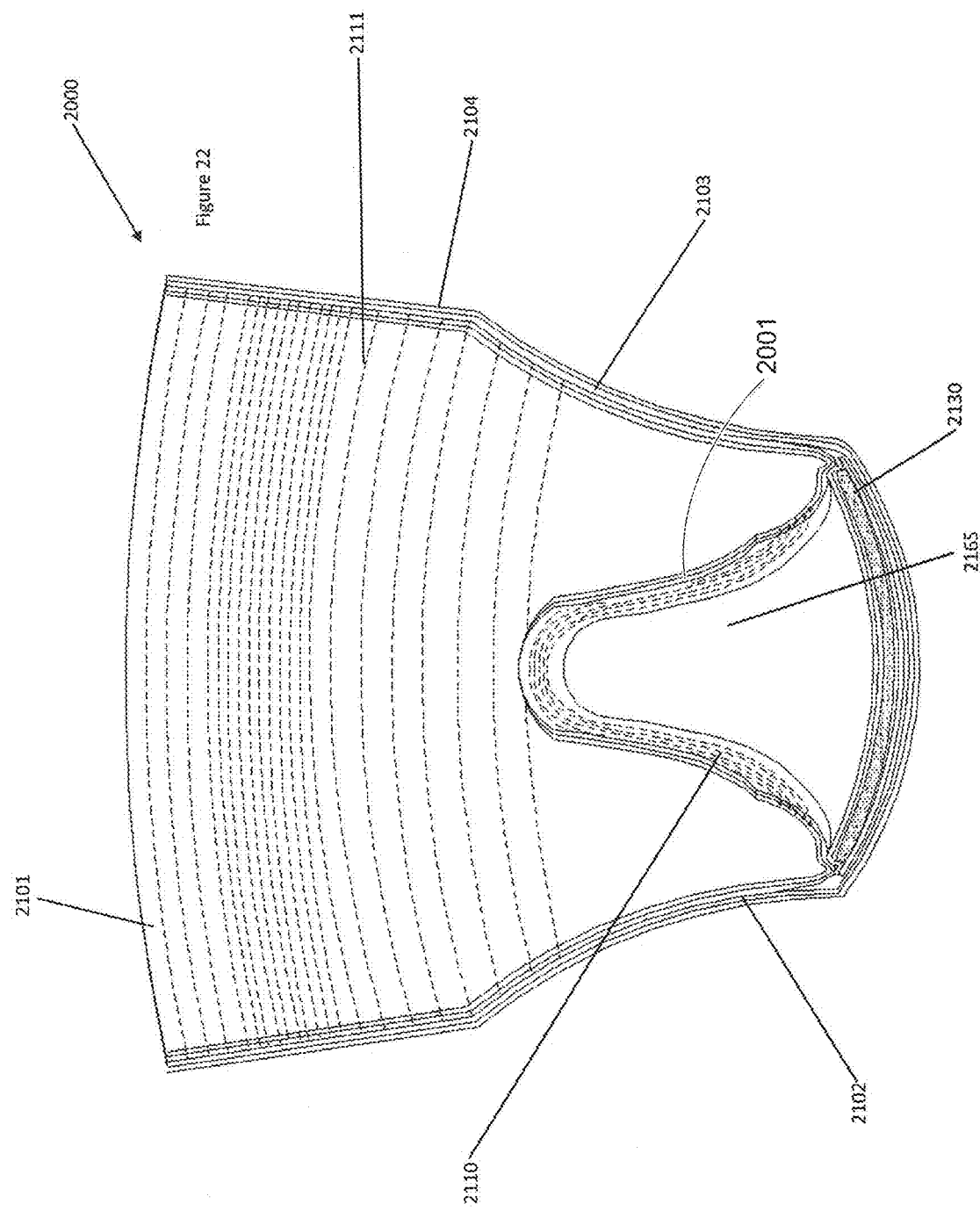
FIG. 22 is a cross-sectional view, along line Y-Y, of the absorbent article of FIG. 19.

FIG. 21 is a cross-sectional view of absorbent article 2000, and FIG. 22 is another cross-sectional view of absorbent article 2000. In FIG. 21, lateral side seam 2150 is shown, which is formed by joining two lateral edges 2151a, 2151b (shown in FIG. 19). Portions of cuff 2001 are depicted. The portion of inner elasticized construction that forms cuff 2001 is unbounded to absorbent member 2130 and the outer elasticized construction, allowing this portion of the inner elasticized construction to be biased upwards (e.g., curl upwards) relative to the absorbent member 2130 and the outer elasticized construction, forming cuff 2001. In some aspects, cutting openings 2165 into the inner elasticized construction reduces resistance from the inner elasticized construction to such upwards biasing (i.e., curling).

Figure 23:
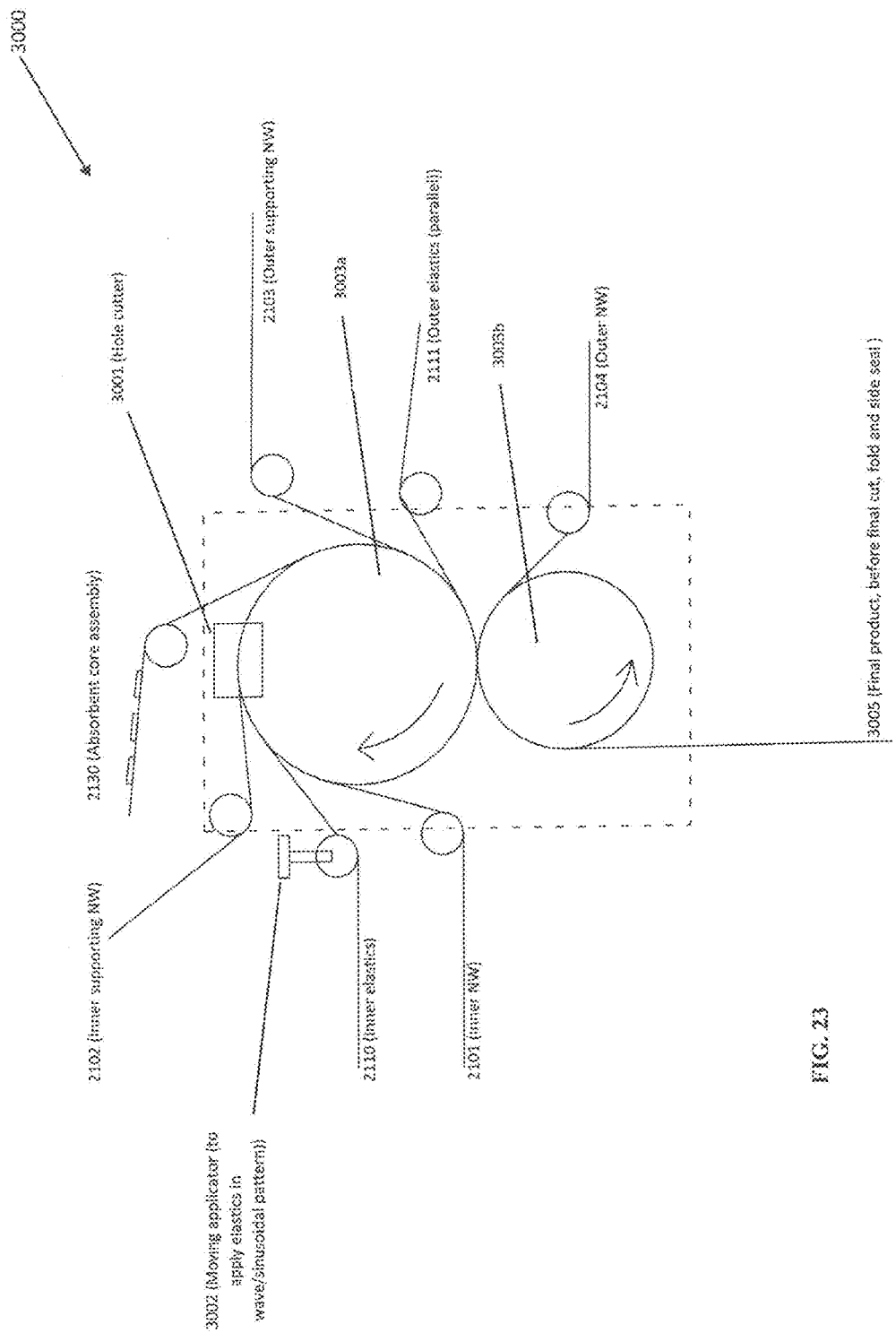
FIG. 23 is a schematic of a system suitable for production of the absorbent article of FIG. 19, in accordance with certain embodiments of the present disclosure.

FIG. 23 is a schematic of a system 3000 suitable for production of the absorbent article of FIG. 19, in accordance with certain embodiments of the present disclosure. In the operation of system 3000, inner sheet 2101, sets of elastic strands 2110a, 2110b, and inner support sheet 2102 may be joined together using form roller 3003a. Elastics guide 3002 (e.g., a moving applicator) may be used to apply sets of elastic strands 2110a, 2110b in a pattern between inner sheet 2101 and inner support sheet 2102. Hole cutter 3001 may then be used to form openings 2165a and 2165b, forming the inner elasticized construction, after which absorbent member 2130, outer support sheet 2103, and elastic strands 2111 may be joined with the inner elasticized construction using form roller 3003a. Outer sheet 2104 may then be joined to elastic strands 2111 and outer support sheet 2103 using form roller 3003b, forming composite product 3005. Composite product 3005 may be subsequently cut, folded and sealed to form absorbent article 2000. One skilled in the art would understand that other systems (or arrangements of system 3000) may be used to form composite product 3005. In some aspects, a web of the outer elasticated construction is formed in the same or similar manner as web 240 as described with reference to FIG. 4 and, after placement of the absorbent member onto the outer elasticated construction but prior to cutting the leg holes (holes 204 as shown in FIG. 4), the inner elasticated construction is placed onto and over the absorbent member and the elasticated construction (e.g., at point 2199 as indicated in FIG. 4), preferably from above the web of the outer elasticated construction. The production of the inner elasticated construction and the outer elasticated construction may thus be synchronized with one another, and may be a constant, linear, machine direction process.

The present disclosure also incorporates by reference the disclosures of each of PCT Publication No. WO2016138466A1 and US 2016/0278999A1, both of which claim priority to U.S. Provisional Application No. 62/121,399, filed Feb. 26, 2015 (also incorporated by reference). These patent applications share one or more common inventors and\or Assignees with the present application and disclosure. Among other things, these referenced documents serve as background for some of the concepts discussed herein. Concepts and descriptions available in these publicly available disclosures may also be referenced and form parts of the concept or aspects of the concepts contemplated and introduced herein, even if not reproduced herein in their entirety. Accordingly, these documents, including the specification, drawings, claims etc., contained therein and which provide form to these disclosures, are hereby incorporated in their entirety and made a part of the present disclosure.

FIGS. 24A-24F are simplified illustrations of an absorbent member or core and a method of making and shaping such a core for integration or incorporation with or into any chassis or absorbent articles, including those described herein with respect to any one of FIGS. 1-23. Exemplary absorbent cores suitable for shaping as described in reference to FIGS. 24A-24F include generally rectangular, wafer-like core sections. For example, MEGATHIN core composites, referred to or described in U.S. Pat. Nos. 6,790,798, 6,794,557, and 8,785,715 (each of which is hereby incorporated by reference in its entirety and made a part of the present disclosure) may be used as the absorbent core due to various qualities thereof, including firmness, ability to fold or shape, as well as thinness. Such a core composite is illustrated in FIGS. 24A-24F. Also, the slitting and folding methods described in U.S. Pat. No. 8,785,715 may be used to slit and fold the absorbent core of FIGS. 24A-24F.

FIG. 24A depicts absorber core 2430. Absorbent core 2430 may be a single layer core or a multilayer core (e.g., double layer core), and may have any desired thickness, width, and length, depending on the particular application. For example and without limitation, absorbent core 2430 may be a single layer core that is less than 6 mm thick or less than 4 mm thick, and more than about 2.0 mm thick. One exemplary single layer core has a thickness of about 2.2 mm thick. Absorbent core may be a double layer core composite, with each layer of the composite having a thickness of less than 5 mm or 6 mm, such as a thickness of between 2 mm and 4 mm. In one exemplary double layer core, each layer of the composite has a thickness of about 2.2 mm. The surface area, lateral expanse, and longitudinal expanse of the absorbent core composite may vary, as with any conventional absorbent article; however, core composite dimensions suitable for embodiments described herein include those that are typical of conventional absorbent articles. For example and without limitation, a typical diaper is about 360 mm long and about 120 mm wide.

With reference to FIG. 24B, absorbent core 2430a is slit at slits 2400, forming slitted core 2430b. After slitting absorbent core 2430a, the portion of slitted core 2430b between slits 2400 (folded core sections 2420, as shown in FIG. 24D) is folded along fold line 2401, as shown in FIG. 24C, forming folded core 2430c.

With reference to FIG. 24D, elastics 2410 are engaged (e.g., bonded with, adhered to, or otherwise attached) with folded core 2430c, forming elasticated core 2430d. Elastics 2410 engaging folded core sections 2420 may be of higher denier than other elastics engaged with elasticated core 2430d, so as to facilitate the desired urging or bias of the folded core sections 2420. In some embodiments, differential tension may be presented on or by the elastics 2410 to folded core sections 2420 to uplift folded core sections 2420. For example, one or more of the elastic strands coupled with the absorbent core (e.g., the outermost elastic attached thereto, closest to the side margins 2432) may be of a higher denier than the other elastic strands attached to other portions of the absorbent core, or two or more of such elastic strands may be positioned closer to adjacent elastic strands than the remaining elastic strands coupled to the absorbent core to provide additional elastic force per unit of surface area to the folded core sections 2420 in comparison to the elastic force per unit area of surface area provided to other sections of the absorbent core.

Figure 24F:
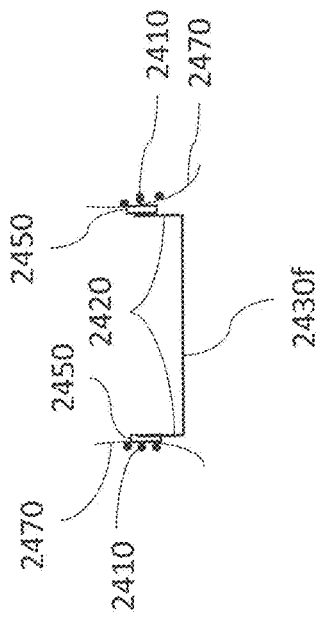
FIG. 24F is a side view of an elasticated absorbent member or core with folds.

When elastics 2410 are released in a relaxed state (as shown in FIG. 24D), elastics 2410 impart force to folded core sections 2420, uplifting folded core sections 2420 relative to the plane defined by the top surface 2431 of elasticated core 2430d. This uplifting of folded core sections 2420 may provide elasticated core 2430d with an hourglass shape (as shown in FIG. 24D). In some aspects, elasticated core 2430d is elasticized by elastics that are not a part of the core (e.g., are not directly attached to the core). For example, elastics 2410 may be attached to a chassis layer 2470 (e.g., a nonwoven) that is adhered to absorbent core 2430f via adhesive 2450, as shown in FIG. 24F. In such embodiments, elastic forces to bias folded core sections 2420 may be imparted by elastics from other, adjacent components of an absorbent article within which the absorbent core is incorporated (e.g., a chassis supporting an elastic construction or an elasticized chassis). In some such embodiments, the elastics urge the folded core sections 2420 outwardly, toward the side margins 2432 of the absorbent core, and away from the top, planar surface 2431 of the core. The folded sections 2420 is thus a portion of the absorbent core that is biased to form an uplifted part of the core or a functional cuff of the core. Such a cuff is an integral part of the absorbent core, rather than a separate attached piece (e.g., a leg cuff with elastics integrated therewith). In this respect, the absorbent core may be free of an elasticized leg cuff, or at least free of an elasticized leg cuff that is separately incorporated therewith or attached thereto. As shown, elasticized absorbent core 2430 has a partial cuff or peripheral barrier or dam formed by uplifted folded core sections 2420, rather than cuff, barrier or dam that fully or continuous surrounds the absorbent core (i.e., as shown, the folded core sections 2420 do not form a 3600 cuff). While shown as including two folded core sections 2420 along a portion of two edges 2432, one skilled in the art would understand that additional slits and additional folded core sections may be provided to form additional cuffs, barriers or dams. In some aspects, core 2430d includes an opening 2465 formed therethrough, about which elastics 2410 are positioned.

Figure 24E:
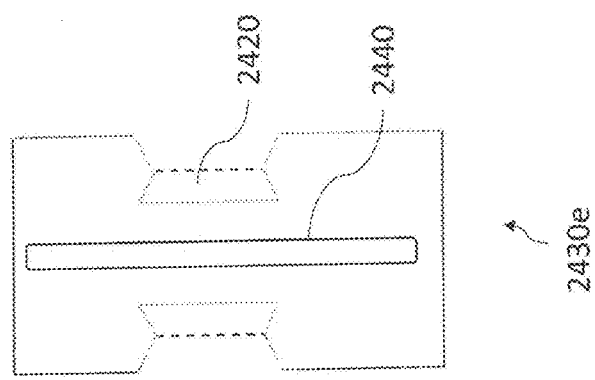
FIG. 24E is an illustration of an absorbent member or core with a fluid distribution channel.

FIG. 24E depicts an alternate core 2430e provided with an absorbent particle/SAP-free lane or channel (channel 2440). Channel 2440 may be positioned centrally on core 2430e and coincident with the primary areas of insult of core 2430c. Channel 2440 facilitates fluid distribution across and about core 2430e. Core 2430e includes folded core sections 2420, which are folded inwardly toward the center of core 2430e and toward channel 2440, providing core 2430e with an hourglass shape. Additionally, as described above, when folded upwards as shown, folded core sections 2420 act as cuffs, barriers, dams, and\or bumpers to prevent side leakage from the core 2430e. Additionally, when folded upwards as shown, folded core sections 2420 increases the basis weight of core 2430e at the central region or central crotch area of core 2430e, which is the primary target zone (i.e., primary area of insult) of core 2430e, thus providing core 2430e with additional absorbency where absorbency is most typically needed.

Embodiments of the present disclosure may utilize core composites that are cuff-less. As used herein, a "cuff-less" core refers to a core to which separate leg cuffs are not attached, as a separate piece (typically elasticized leg cuffs). One beneficial result is an absorbent structure with a larger "bucket" or "reservoir" for liquid receipt. A larger bucket provides capacity to handle larger volumes of insult without leaking, such that the core area has time to absorb the insult. This "bucket" (integrated barrier cuffs or cuffs as provided by the uplifted folded core sections) is sealed against the body during wear, similar to leg cuffs but more robust, firm, and uniform, and with greater capacity due to its more outwardly or outer location. As the bucket is an integrated part of the absorbent core, the bucket presents less stress, less leakage, and less failure points to the absorbent core than would a separately attached cuff. Additionally, as the bucket is formed of portions of the absorbent core, the bucket exhibits absorbent properties. Traditional leg cuffs may not effectively prevent leakage through the front or back of an absorbent article, or crotch and waist regions of the absorbent core (as opposed to the lateral or side margins). In fact, a separate dam or barrier is often attached or otherwise created and placed at the front and back (waist end regions) of the absorbent article. In some embodiments of the present disclosure, a continuous or 360 degree cuff is provided (either as disclosed in FIGS. 19-23 or as disclosed in FIGS. 24A-24F) that completely surrounds the core and acts to prevent leakage from the side or lateral margins as well as the front and back waist end regions. Such a continuous cuff structure is a functional replacement for both a pair of parallel leg cuffs attached to the core surface and a pair of end dams provided at the waist end regions. Such single, continuous core cuffs provide a manner of adding a leg cuff to a core product, and may function more effectively than conventional leg cuffs and\or end dams in several respects. The embodiments cores 2430a-2430f, as shown in FIGS. 24D-24F are elasticized cores with integrated, elasticized core cuffs. The various embodiment of cores depicted in FIGS. 24A-24F may be used as the absorbent member (or a portion thereof) in any of the embodiments that include an absorbent member depicted in FIGS. 1-23.

Referring to the Figures, particularly FIGS. 19-24F, an absorbent article according to the disclosure includes a multilayer bodyside chassis having an inner elastic construction sandwiched between a first fabric layer and second fabric layer; a multilayer outer chassis having an outer elastic construction; and an absorbent member (or absorbent core) positioned between the multilayer bodyside chassis and the multilayer outer chassis. The core may be in a variety of shapes known in the art but generally is elongated, having a (longitudinal) length (from one end edge "B" and the end region proximate that end to the opposite end edge "C" and end region proximate thereto) that is greater than the lateral width (side edge or margin "E" to opposite side edge or side margin "D"). For clarity, the end edge regions, in this respect, is coincident with and equal to what are commonly known, as well, as waist or waist end regions. The article also has an inner elastic construction that, for present purposes, means the arrangement of elastics or elastic members (e.g., strands) situated relative to and supported within one or more fabrics or material layers (i.e., nonwoven layers). As described and shown herein, the elastics are disposed and supported within the first and second fabric layers so as to form, therewith, an (elastic or elasticized) annular cuff projected above the absorbent member. See e.g. FIG. 20. As used herein, the term "cuff" in this respect means material that projects from, turns back, or protrudes away from another surface. As shown in these FIGURES, the part that is the "cuff" is the portion that is separate from and is spaced upwardly from the core or other surface below it. The elastic annular cuff may be described as the portion wherein the elastics are disposed and to which the elastics directly imparts a force or bias to.

In FIGS. 20-20C, the opening 2165 is described as being positioned inwardly of the inner elastic construction or annular cuff. That is the opening 2165 is closer to the center of the article and the core than is the cuff. Also, the annular cuff in these Figures is described as encircling a central portion of the absorbent member inward of a periphery of the absorbent member. The term "periphery", in this respect, refers to the outer edge of the core.

Furthermore, the inner elastic construction is also described as having at least two sets of elastic distributions containing a plurality of spaced apart elastics. The elastic distributions refer to a group of elastics that, as described in respect to FIGS. 1-18, of example, are continuous in the region of interest, commonly sourced, and traverse generally together from one margin of the article or chassis that make up the article to another margin. Notably, the annular cuff may comprise or consist of elastics sourced from two different elastic distributions.

In another aspect, the absorbent article is described as having a bonded region, wherein a multilayer bodyside chassis is bonded with a multilayer outer chassis and/or the absorbent member, and in an unbonded region, wherein the multilayer bodyside chassis is detached the multilayer outer chassis and is detached from the absorbent member and is movable away therefrom. Such bonded or unbonded regions may be identified with either or both chassis or with the article (where the chassis is located). For example, the article may have an unbonded region, as it pertains to the chassis, wherein the chassis is not bonded to any other component and can be moved relative to that component to create a space or gap therebetween (where the space is at least partially defined by the height 2179 and angle 2177). As such, an annular cuff is formed that projects above and away relative to the absorbent member 2130 (e.g., the annular cuff extends away inward and/or outward relative to absorbent member 2130).

Notably, the annular (elastic and elasticized) cuff in FIG. 20 is located the unbonded region (of the chassis or of the article), and is said to be movable from the absorbent member to provide a three-dimensional space therebetween. Accordingly, that space has volume and has a depth (height 2179) and lateral and longitudinal expanse. As shown in FIG. 20C, for example, the unbonded region (2163) of the article extends outside of the annular cuff and has an outside periphery spaced laterally and longitudinally from the annular cuff. The back wall of the voluminous space is, therefore, outward of the cuff and is coincident with the inside periphery of the bonded region 2161 (where the bonded region starts or where the bodyside chassis is bonded to the core or the outer chassis). For illustration, the absorbent article is later shown to be continuously (optionally uniformly) bonded in the bonded region. That is the bonded region is continuous (but in practice, may not be completely solid, i.e., where every square cm of the bodyside chassis is bonded to the outer chassis or core).

Preferably, the inside periphery of the bonded region is mostly on the core or high enough on the chassis or article (when the article is worn) where fluid does not typically travel. This mitigates the risk of fluid leakage. Notably, the elastics of the outer chassis traverse opposite end regions of the core. When the article is worn, these end regions are situated high around the wearer, in and around the waist regions. The sets of elastics are encouraged by, and further enhances, the bend and curvature in the core (as shown in some of the perspective views of FIGS. 19-24 (21-22)). The two elastic regions act on the ends of the core, thereby rotating it and creating a moment about a line near the lateral centerline.

The foregoing description has been presented for purposes of illustration and description. It is to be noted that the description is not intended to limit the embodiments to the various articles, products, systems, apparatus, and processes disclosed herein. Various aspects of the embodiments as described above may be applicable to other types of disposable absorbent articles and garments, and processes for making the same. For example, the elastic composite described above, may be incorporated in other disposable absorbent garments such as diapers, etc. or in other areas or as other components of the garment. Moreover, the processes described herein may be utilized to produce compositions, garments and articles other than those described herein. Such variations will become apparent to one skilled in the relevant consumer products are provided with the present disclosure. Consequently, variations and modifications commensurate with the above teachings, and the skill and knowledge of the relevant art, are within the scope of the present disclosure. The embodiments described and illustrated herein are further intended to explain the best modes for practicing the embodiments, and to enable others skilled in the art to utilize the embodiments, with various modifications required by the particular applications or uses of the present embodiments.

What is claimed is:

1. An absorbent article, the absorbent article comprising:
an absorbent core comprising absorbent material, wherein the absorbent core has a first slit, a second slit, and a first fold line;
elastics coupled with the absorbent core;
wherein the elastics bias a portion of the absorbent core to fold along the first fold line, forming a first folded core section of the absorbent core, wherein the first folded core section is positioned between the first and second slits in the absorbent core, and wherein the first folded core section forms a first cuff of the absorbent core.

2. The absorbent article of claim 1, wherein the absorbent core has a first lateral side edge, a second lateral side edge, and a central region between the first and second lateral side edges, and wherein the first and second slits extend from the first lateral side edge toward the central region.

3. The absorbent article of claim 2, further comprising a third slit and a fourth slit in the absorbent core and a second fold line, wherein the third and fourth slits extend from the second lateral side edge toward the central region, wherein the elastics bias a portion of the absorbent core to fold along the second fold line, forming a second folded core section of the absorbent core, wherein the second folded core section is positioned between the third and fourth slits in the absorbent core, and wherein the second folded core section forms a second cuff of the absorbent core.

4. The absorbent article of claim 3, further comprising a fluid distribution channel within the absorbent core, wherein the fluid distribution channel is positioned in the central region between the first and second cuffs.

5. The absorbent article of claim 4, wherein the first and second folded core sections are both folded inwardly toward the central region of the absorbent core and toward the fluid distribution channel.

6. The absorbent article of claim 3, wherein the elastics that are coupled with the first and second folded core sections have a higher denier and higher tension than elastics coupled with other portions of the absorbent core.

7. The absorbent article of claim 3, wherein the first and second folded core sections are uplifted by the elastics to a position above a top surface of the absorbent core, and wherein the first and second folded core sections form peripheral barriers on the absorbent core.

8. The absorbent article of claim 3, further comprising an opening in the central region of the absorbent core, wherein the elastics are positioned about the opening.

9. The absorbent article of claim 3, wherein the first and second cuffs comprise absorbent material.

10. The absorbent article of claim 3, wherein the absorbent core is a single layer absorbent core.

11. The absorbent article of claim 3, wherein the absorbent core is a multilayer absorbent core.

12. The absorbent article of claim 1, further comprising a topsheet and a backsheet, wherein the absorbent core is positioned between the topsheet and the backsheet.

13. A method of making an absorbent core, the method comprising:
slitting an absorbent core at two locations to form a first slit and a second slit in the absorbent core; and
coupling elastics with the absorbent core, wherein the elastics bias a first portion of the absorbent core positioned between the first and second slits to fold along a first fold line as a first folded core section, wherein the first folded core section forms a first cuff of the absorbent core.

14. The method of claim 13, wherein the absorbent core has a first lateral side edge, a second lateral side edge, and a central region between the first and second lateral side edges, and wherein the first and second slits extend from the first lateral side edge toward the central region.

15. The method of claim 14, further comprising slitting the absorbent core to form a third slit and a fourth slit in the absorbent core, wherein the elastics bias a second portion of the absorbent core positioned between third and fourth slits to fold along a second fold line as a second folded core section, wherein the second folded core section forms a second cuff of the absorbent core.

16. The method of claim 15, further comprising providing a fluid distribution channel within the absorbent core, wherein the fluid distribution channel is positioned in the central region between the first and second cuffs.

17. The method of claim 16, wherein the first and second folded core sections are both folded inwardly toward the central region of the absorbent core and toward the fluid distribution channel.

18. The method of claim 15, wherein coupling the elastics comprises coupling first elastics with the first folded core section and coupling second elastics with a remainder of the absorbent core, wherein the first elastics have a higher denier than the second elastics.

19. The method of claim 15, wherein biasing the first and second portions of the absorbent core to fold along the first and second fold lines includes releasing tension on the elastics such that the elastics enter a relaxed state.

20. The method of claim 15, wherein biasing the first and second portions of the absorbent core comprises uplifting the first and second portions relative to a plane defined by a top surface of a remainder of the absorbent core.

21. The method of claim 15, further comprising forming an opening in central region of the absorbent core, wherein the elastics are positioned about the opening.

22. The method of claim 15, further positioning the absorbent core between a topsheet and a backsheet.

23. An absorbent article having cuffs integrated into an absorbent core, the absorbent article comprising:
an absorbent core comprising absorbent material, the absorbent core having a first lateral edge, a second lateral edge, and a central region between the first and second lateral edges;
a first slit and a second slit in the absorbent core, wherein the first and second slits extend from the first lateral side edge toward the central region;
a third slit and a fourth slit in the absorbent core, wherein the third and fourth slits extend from the second lateral side edge toward the central region;
a first fold line in the absorbent core and a second fold line in the absorbent core;
a plurality of elastics coupled with the absorbent core;
wherein the elastics bias a first portion of the absorbent core between the first and second slits to fold along the first fold line, forming a first folded core section of the absorbent core, and wherein the first folded core section forms a first cuff of the absorbent core;
wherein the elastics bias a second portion of the absorbent core between the third and fourth slits to fold along the second fold line, forming a second folded core section of the absorbent core, and wherein the second folded core section forms a second cuff of the absorbent core;
wherein the first and second folded core sections both project upward from a top surface of a remainder of the absorbent core and toward the central region of the absorbent core; and
wherein the first and second cuffs comprise absorbent material.

* * * * *